US007117227B2

(12) United States Patent
Call

(10) Patent No.: US 7,117,227 B2
(45) Date of Patent: Oct. 3, 2006

(54) METHODS AND APPARATUS FOR USING THE INTERNET DOMAIN NAME SYSTEM TO DISSEMINATE PRODUCT INFORMATION

(76) Inventor: Charles G. Call, 68 Horse Pond Rd., West Yarmouth, MA (US) 02673

( * ) Notice: Subject to any disclaimer, the term of this patent is extended or adjusted under 35 U.S.C. 154(b) by 354 days.

(21) Appl. No.: 10/139,421

(22) Filed: May 6, 2002

(65) Prior Publication Data

US 2002/0161745 A1 Oct. 31, 2002

Related U.S. Application Data

(60) Continuation-in-part of application No. 09/621,662, filed on Jul. 24, 2000, now Pat. No. 6,418,441, which is a division of application No. 09/316,597, filed on May 21, 1999, now Pat. No. 6,154,738, which is a continuation-in-part of application No. 09/049,426, filed on Mar. 27, 1998, now Pat. No. 5,913,210.

(51) Int. Cl.
*F06F 7/00* (2006.01)
*G06F 17/30* (2006.01)

(52) U.S. Cl. .................................... 707/104.1; 707/101

(58) Field of Classification Search ......... 707/1–104.1, 707/205; 705/1, 14, 23, 20, 26–27, 29, 50–51, 705/59, 77–78, 8; 709/200–206, 213–219, 709/223–225; 235/375, 383; 717/100, 124; 714/1, 25, 37; 379/90.01–93; 713/100, 713/200; 703/1–104.1
See application file for complete search history.

(56) References Cited

U.S. PATENT DOCUMENTS 5,793,966 A * 8/1998 Amstein et al. ............. 709/203
5,950,173 A * 9/1999 Perkowski ................... 705/26
6,075,783 A * 6/2000 Voit ........................... 370/352
6,098,106 A * 8/2000 Philyaw et al. .............. 709/238
6,199,048 B1 * 3/2001 Hudetz et al. ................ 705/23
6,201,965 B1 * 3/2001 Mizell et al. ................ 455/433

(Continued)

FOREIGN PATENT DOCUMENTS

WO     WO9806055    * 2/1998

(Continued)

OTHER PUBLICATIONS

Network Solutions, the dot com people, "Get a Web Address or search our database for availability", Apr. 27, 1999, 2 pages.*

(Continued)

*Primary Examiner*—Don Wong
*Assistant Examiner*—Linh Black

(57) ABSTRACT

Methods and apparatus for disseminating over the Internet product information produced and maintained by product manufacturers using existing universal product codes (bar codes) as access keys. A cross-referencing resource preferably implemented by the existing Internet Domain Name System (DNS) receives Internet request messages containing all or part of a universal product code value and returns the Internet address at which data or services relating to the identified product, or to the manufacturer of that product, may be obtained. By using preferred Web data storage formats and protocol which conform to XML, XLS, XLink, Xpointer, RDF and Web service standards specifications, product and company information may be seamlessly identified, retrieved and integrated with information from other sources. A "web register" module can be employed to provide an Internet interface between a shared sales Internet server and an otherwise conventional inventory control system, and operates in conjunction with the cross-referencing server to provide detailed product information to Internet shoppers who may purchase goods from existing stores via the Internet.

24 Claims, 11 Drawing Sheets

U.S. PATENT DOCUMENTS

| | | | | |
|---|---|---|---|---|
| 6,202,207 B1 * | 3/2001 | Donohue | | 717/173 |
| 6,275,574 B1 * | 8/2001 | Oran | | 379/201.01 |
| 6,303,086 B1 * | 10/2001 | Heimer | | 422/186.3 |
| 6,314,457 B1 * | 11/2001 | Schena et al. | | 709/219 |
| 6,484,149 B1 * | 11/2002 | Jammes et al. | | 705/26 |
| 6,542,933 B1 * | 4/2003 | Durst et al. | | 709/229 |
| 6,549,933 B1 * | 4/2003 | Barrett et al. | | 709/203 |
| 6,614,774 B1 * | 9/2003 | Wang | | 370/338 |
| 2002/0184237 A1 * | 12/2002 | McFeely | | 707/104.1 |
| 2003/0217140 A1 * | 11/2003 | Burbeck et al. | | 709/224 |

FOREIGN PATENT DOCUMENTS

| | | | |
|---|---|---|---|
| WO | WO9904326 | * | 1/1999 |

OTHER PUBLICATIONS

"W3C, XSL Transformations (XSLT) Specification Version 1.0", W3C Working Draft, Apr. 21, 1999, pp. 1-20. (www.w3.org/TR/1999/WD-xslt-19990421).*

Joseph T. Foley, "An infrastructure fore Electromechnical Appliances on the Internet," dated May 1999, Jul. 15, 1999, 74 pages, M.I.T. Master's thesis, Cambridge, MA., pp. 2-74.

Sanjay Sarma, David L. Brock & Kevin Ashton, "The Networked Physical World," Oct. 1, 2000, Restricted until Jan. 1, 2001, 16 pages, M.I.T. Auto-ID Center, Cambridge, MA, pp. 1-16.

David L. Brock, "The Electronic Product Code (EPC)," Jan. 1, 2001 restricted until Apr. 1, 2001, 21 pages, M.I.T. Auto-ID Center, Cambridge, MA.

David L. Brock, "The Physical Markup Language," Feb. 2001, 9 pages, M.I.T. Auto-ID Center, Cambridge, MA., 9 pages, (I-VI).

* cited by examiner

METHODS AND APPARATUS FOR USING THE INTERNET DOMAIN NAME SYSTEM TO DISSEMINATE PRODUCT INFORMATION

CROSS-REFERENCE TO RELATED APPLICATIONS

This is a continuation in part of U.S. application Ser. No. 09/621,662 filed on Jul. 24, 2000 (now U.S. Pat. No. 6,418,441 issued Jul. 9, 2002), which was a division of U.S. application Ser. No. 09/316,597 filed on May 21, 1999 (now U.S. Pat. No. 6,154,738 issued on Nov. 28, 2000), which was a continuation in part of U.S. application Ser. No. 09/049,426 filed on Mar. 27, 1998 entitled "Methods and Apparatus for Disseminating Product Information via the Internet" ( now U.S. Pat. No. 5,913,210 issued on Jun. 15, 1999). This application claims the benefit of the filing dates of each of the foregoing applications, and incorporates the disclosure of each of the foregoing patents and applications herein by reference.

FIELD OF THE INVENTION

This invention relates to methods and apparatus for transferring requests for specific information to preferred sources of that information on the Internet.

BACKGROUND AND SUMMARY OF THE INVENTION

Manufacturers must provide information about their products to resellers, consumers, and others. Resellers need product information to select, promote and support the products they distribute. Consumers need information about available products to make informed buying choices. Advertisers, product analysts, manufacturer's representatives, shippers, and others also need information about the goods with which they deal.

Under current practices, product information typically originates with manufacturers and is primarily distributed in conventional print media advertising and product packaging. This information is often incomplete, difficult to update, and available only to a limited distribution. While the advent of the World Wide Web has permitted manufacturers to make detailed, up-to-date product information available via the Internet, the information describing a specific product is often difficult to locate, particularly when the URL (uniform resource locator) of the manufacturer's website is not known.

It is a general object of the present invention to transfer a request for information specified by an identifier, such as a product code, to a preferred source of that information, such as an Internet information resource devoted to the product specified by the product code which is created and maintained by the product's manufacturer.

The preferred embodiment of the present invention employs an Internet resource, called a "product code translator" that is preferrably implemented using the existing Internet Domain Name System for storing cross-references between universal product codes identifying specific products and Internet addresses specifying the locations at which information about these products may be obtained. The cross-references specify the universal product codes assigned to the participating manufacturers, such as Global Trade Item Numbers in the EAN-UCC system widely used in retail stores for barcode scanning at checkout counters, and the Internet addresses where information can be obtained about the products designated by those codes.

A preferred embodiment of the present invention takes the form of a system for disseminating information relating to different manufactured products each of which is designated by a unique universal product code value. The system employs different host computers for storing information about the products. Each computer supports an entry point connection to the Internet that is uniquely identified by an Internet protocol address for receiving and responding to Internet messages requesting information relating to one or more of the products. The server administrators register cross-references in the Internet Domain Name System. Each cross-reference specifies an association between an alphanumeric product code domain name and a corresponding Internet protocol address. The alphanumeric product code domain name is a character string whose content may be completely derived from a specific universal product code value using a predetermined transformation process. The cross-referenced corresponding Internet protocol address identifies the particular entry point connection that receives and responds to Internet messages requesting information relating to a product designated by the specific universal product code value.

Thereafter, any user connected to the Internet may retrieve information or invoke services relating to a product designated by a selected universal product code value. The user derives a target product code domain name character string from the selected universal product code value using the predetermined transformation process, and transmits the target product code domain name to the Internet Domain Name System to obtain the corresponding target Internet protocol address specified by one of the registered cross-references. The user then transmits an Internet message requesting information relating to the selected products to the target Internet protocol address.

The request message contains a Universal Resource Identifier (URI) which includes the target product code domain name character string and which identifies the specific resource reqeusted. The host designated by the Internet protocol address interprets the URI to provide the data or service specified by the URI. The identity and invocation mechanism (binding specification) for resources available at a given host may be specifed by resource description files which may be accessed at predetermined location at the host specified by the target domain name. These resource description files may advantageously include Web Service Inspection Language and Web Service Description Language documents which identify and describe product and company related Web services available at each host.

These and other objects, features and advantages of the present invention will be made more apparent through a consideration of the following detailed description of a preferred embodiment of the invention. In the course of this description, frequent reference will be made to the attached drawings.

DETAILED DESCRIPTION

Figure 1:
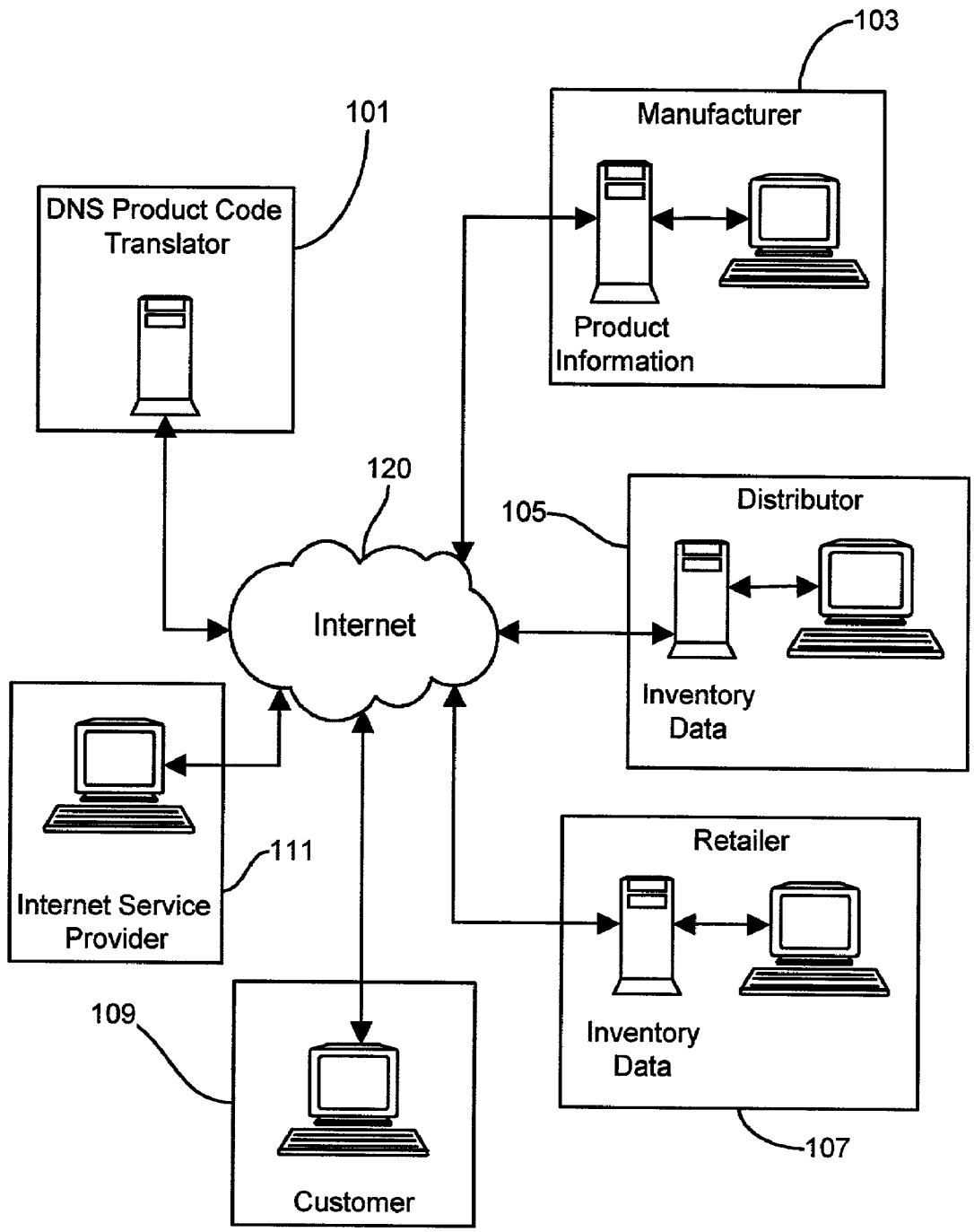
FIG. 1 is a schematic block diagram illustrating various instrumentalities which make use of the invention interconnected via the Internet.

The preferred embodiment of the present invention takes advantage of three existing and highly successful technologies: the Internet, the Internet Domain Name System (DNS), and the EAN-UCC universal product code system. In accordance with the present invention, the Internet and the DNS are employed to provide low cost, worldwide, bidirectional communication which enables product information to be requested by and sent to any person or firm using one or more universal product codes as information access keys. The universal product code system is in widespread use to uniquely identify each of the thousands of different suppliers and millions of different items that are warehoused, sold, delivered and billed throughout commercial channels of distribution. In accordance with the invention, the Internet Domain Name System is used in a new way to act as a product code translator for resolving domain names containing all or part of a universal product code into a cross-referenced Internet addresses from which information and services relating to the products specified by those product codes may be obtained.

The present invention enables the retrieval of information about products from the source of those products, typically the manufacturer, by those who need that information, such as resellers and consumers. In accordance with the invention, any person or firm having access to the Internet and knowing the universal product code for a product may obtain information about that product from the participating manufacturer which supplies that product. The system employs the DNS as a product code translator, which is implemented by a plurality of distributed name servers but which is illustrated by the single resource seen at 101 in FIG. 1. The DNS product code translator is accessed via the Internet to perform a translation of domain names containing specified universal product codes into the corresponding Internet addresses from which information about the designated products can be obtained.

The product code translator 101 stores cross-references between product codes and Internet addresses. The product codes and the Internet addresses are provided by or on behalf of participating manufacturers and suppliers, such as the manufacturer illustrated at 103 in FIG. 1. These cross-references may then be retrieved from the cross-reference resource 101 by resellers, prospective buyers, as illustrated by the distributor 105, the retailer 107 and the customer 109 seen in FIG. 1. Internet Service Providers, as illustrated by the ISP 111 in FIG. 1, may also utilize the data provided by the product code translator 101 to provide a variety of services and functions.

Before further describing how these entities function within the system, it will be useful to clarify some of the terms which will be used in this specification:

The term "universal product codes" (lower case) is used to indicate standardized industry or inter-industry codes used to designate items, packages and services made, used, leased or sold in commerce. The term thus includes the Universal Product Codes ("U.P.C.s") used by suppliers in the United States and Canada and managed by the Uniform Code Council, Inc., 8163 Old Yankee Road, Dayton, Ohio 45458; the EAN codes used by suppliers outside the U.S. and Canada under the general direction of EAN International, rue Royale 145, 1000 Bruxelles—Belgium; and any other multi-industry or single industry standard product designation system. The fourteen-digit Global Trade Item Number or "GTIN" numbering system is a preferred form of universal product numbering system and subsumes the U.P.C. codes as well as the EAN-13 and SCC-14 codes. In database applications, each of the code values is stored in a standardized form, right justified and zero filled, in a 14 digit field. The final, lowest-order digit of the code is a check digit which is calculated from the higher order digits using a standard algorithm established by the EAN—UCC System (available at http://www.ean-int.org/cdcalcul.html).

The term "manufacturer" will be used to refer to manufacturers, suppliers, vendors, licensors and others to whom sets of universal product codes have been assigned, or their agents. Typically, this assignment takes the form of the designation of a particular value for a portion of the universal product code which is reserved for exclusive use by a particular manufacturer. For example, the entity to which a specific six-digit "company-identifier" portion of a 12-digit numeric U.P.C. code has been assigned is a "manufacturer" as that term is used in this specification. The portion of the universal product code that specifies the product's manufacturer is variously called the "company prefix," the "company code," and the "company identifier."

The term "product" is used to refer to a kind of item which is uniquely identified by a single universal product code, as opposed to a specific individual item of that kind. For example, a specific U.P.C. code is assigned by the manufacturer, Hershey Foods Corp., to 'Reese's Creamy Peanut Butter" as packaged in 510 gram containers (a "product") whereas a different U.P.C. code is assigned to the same brand of peanut butter when packaged in containers of a different size (a different "product").

The term "Internet address" will be used to refer to the all, or a significant part of, a reference to a resource on the Internet. Such a reference may take the form of a numerical IP address or an alphanumeric Uniform Resource Locator ("URL") which may identify a file on a specified machine, a database query, a specific command output, or some other accessible Internet resource. Thus, the term "Internet address" includes such things as a specific 32-bit address of a specific computer connected to the Internet, written in decimal as "123.040.212.002". Alternatively, the term "Internet address" may refer to a domain name such as "patentsoft.com" which can be resolved into a numerical IP-address using a domain name server. In addition, an "Internet address" may take the form of the URL of a file accessible via the Internet, such as "ftp://www.sample.com/directory/filename.xxx"; a URL identifying a query processing script with passed parameters, such as "http://xxx.yyyy-.com/cgi/search%01234567890123"; or an email address such as "847563@manufacturer.com".

The Product Code Translator

Figure 2:
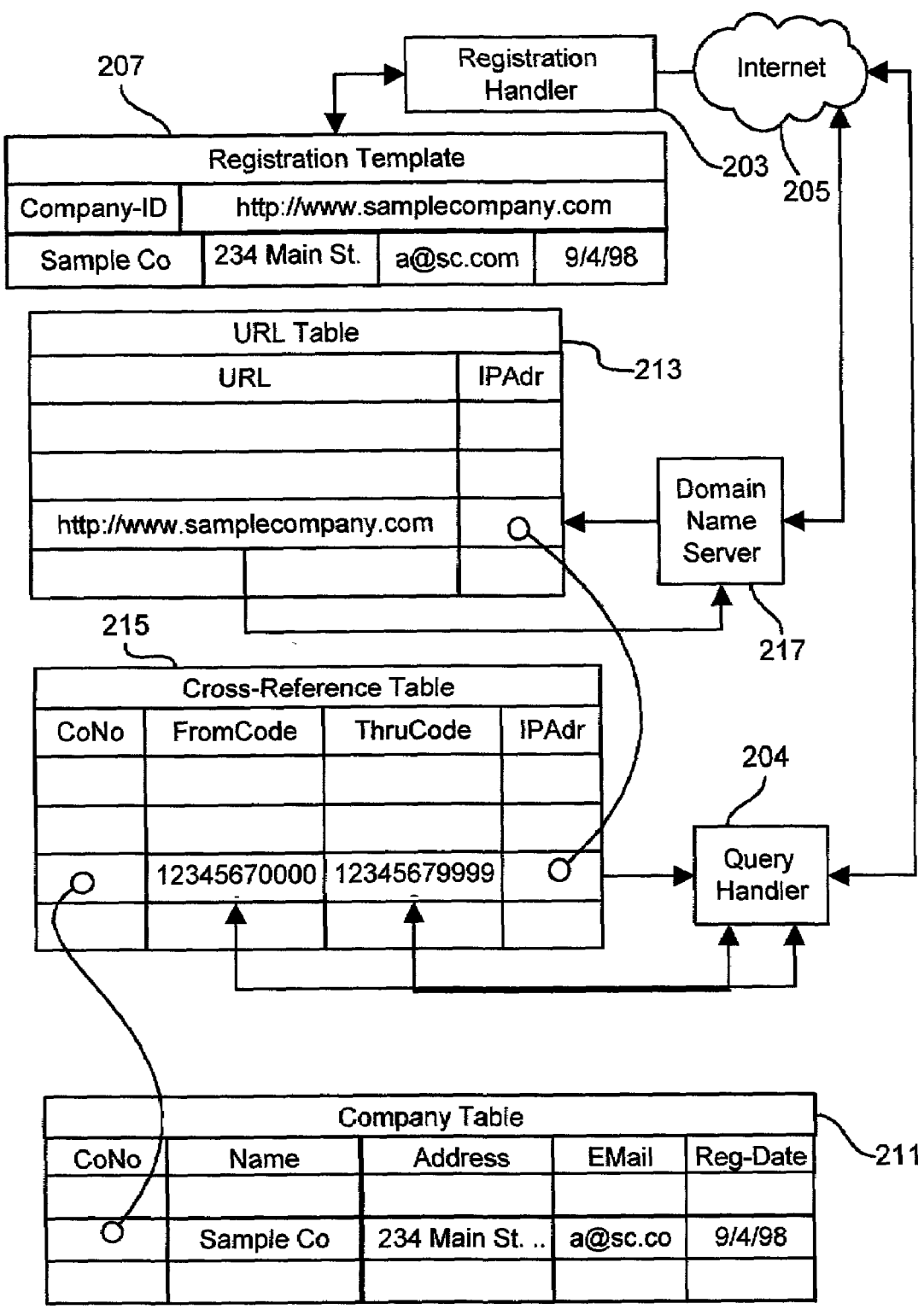
FIG. 2 is a diagram illustrating the interrelationship of the principle data structures used to implement a product code translator of the type contemplated by the invention.

The product code translator seen at 101 in FIG. 1 performs two primary functions illustrated in FIG. 2: (1) its registration handler 203 accepts cross-references submitted by manufacturers which relate their assigned universal product codes to associated Internet addresses where information relating to their products may be obtained, and (2) its query handler 204 accepts queries via the Internet 205, each query including all or part of one or more universal product codes, and returns the Internet addresses which can be used to obtain information about the products identified by those codes. The product code translator 101 may also advantageously perform other functions, examples of which are described below.

In the preferred embodiment of the invention, the existing Internet Domain Name System, including its standard methods of accepting domain name registrations from registrants and for maintaining a distributed, hierarchical mechanism for organizing the name space of the Internet, is used to advantage to perform product code to Internet address translation. However, such functions can also be performed by other means, as illustrated by the example described in conjunction with FIG. 2 of the drawings.

As seen in FIGS. 1 and 2, the product code translator 101 may be advantageously implemented by a server computer which stores information in a relational database consisting of the tables depicted in FIG. 2. If desired, the product code translator 101 may be implemented with a plurality of "mirrored" servers at different locations, or clustered servers at the same location containing the same cross-referencing data to share the processing burden and provide redundant fault-tolerant reliability. In addition, different servers or sets of mirrored or clustered servers may be used to process different assigned subsets of the gamut of universal product codes. Whether one or many servers is used, each may be preferably implemented using conventional server hardware and conventional server operating system software, such as Microsoft NT Server, Netscape Application Server, SCO Unixware, Sun Enterprise Server, and the like.

The registration handler process 203, which may be implemented on a server which stores cross-references, or on a separate server operated by a central registration authority, receives each registration submission via the Internet 205 to create an incoming registration data illustrated by the data template record 207. The registration template record 207 includes several fields: an Company-ID field which holds the company-identifier portion of a universal product code in EAN format; a URL field which holds the Uniform Record Locator constituting the "base address" at which information can be retrieved about products designated by those universal product codes, company information fields which include the company's name, mailing address and email address fields so that the manufacturer submitting the registration can be identified and contacted; and a date field which specifies the date upon which the registration was first made.

The registration handler 203 may obtain the submitted data needed to create the registration template record in a variety of ways, such as accepting a HTML web page form completed and submitted via the Internet by a registrant, processing an incoming email message containing the necessary information, or receiving the needed information by telephone or regular mail.

The registration handler process preferably incorporates a mechanism or procedure for insuring that the registrant has the authority to create and alter the information being supplied. A variety of methods for enhancing the security of the registration process may be employed, including the issuance of a password at the time a range of universal product codes is first registered, with the requirement that the same password be thereafter provided by anyone who seeks to alter the information originally provided with respect to any product code within that previously registered range. The registration procedure may also require each registrant to provide an email contact address to which an email message of predetermined content is sent after the initial registration form is completed, to which the registrant must respond within a predetermined time to verify the registration. Any attempt thereafter to change the contact email address results in a message being sent to the originally registered email contact address advising that an attempt is being made to alter the registration. Finally, email confirmation may be requested from the email address registered with InterNIC for the URL to which universal product codes are to be linked. This step confirms that the person attempting a registration in fact has authority to link to that host computer and provides an additional safeguard against unauthorized submissions.

Instead of maintaining a user name and password database, the registration handler can use a database of certificates, such as Certificate Server available from Netscape, to create, sign, and manage certificates for all participating manufacturers, configuring other servers to accept only authorized user certificates. A scalable database may be used to store the status of each certificate, and the issuance and revocation of certificates can be centrally administered from the product code translator or a separate registration authority. Similar password, certificate or digital signature protection schemes may be used to provide access to certain data or to data in certain forms only to authorized requesters.

The information contained in the incoming registration template 207 is used to create records (rows) in three separate tables in the relational database: a company table 211, a URL table 213 and a cross-reference table 215. As seen in FIG. 2, the company table 211 includes a numerical company number field CoNo which is also present in the cross-reference table 215 so that each cross-reference table row can be related to a particular company description record in the company table which has the same CoNo value. The key field CoNo establishes a one-to-many relationship between the company table 211 and the cross-reference table 215 since a participating company identified by a unique CoNo value may register more than one set of universal product codes, potentially associated with different IP-addresses, requiring more than one row in the cross-reference table 215.

The Company-ID field in the registration template record is used to complete two fields, FromCode and ThruCode, in a row in cross-reference table 215. These fields specify a range of one or more consecutive universal product codes. Both of these two fields preferably stores a 64-bit integer which specifies a 14 decimal digit universal product code called a Global Trade Item Number ("GTIN") drawn from the global pool of 14-digit numbers which includes the U.P.C., EAN-13 and SCC-14 codes. In this way, all three coding systems can be accommodated by the cross-reference table 215; for example, a 12-digit U.P.C. number 7 12345 12345 9 is the same as the 13 digit EAN number 07 12345 12345 9 and the same as the 14 digit SCC-14 number 0 07 12345 12345 9. If the U.P.C. six digit company identifier 7 12345 is specified in the registration template Company-ID field, the FromCode field of the cross-reference table record would be loaded with the number 71234500000 to specify the lowest valued universal product code cross-referenced to the corresponding IP address in the IPAdr field of the table 215, and the ThruCode field would be loaded with 71234599999 to specify the highest valued universal product code cross-referenced to that IP address. The use of the low-value/high-value range specification fields in each row of the cross-reference table 215 permits different ranges of universal product codes having the same Company-ID value to be associated with different Internet addresses in the IPAdr field of the cross-reference table 215, thus enabling a single manufacturer having a single assigned Company-ID value to store information about different products designated by different sets of its universal product codes on different Internet servers, or to cross-reference non-continuous sets of universal product codes to the same or different servers. Note further that a manufacturer need not cross-reference all of its available assigned universal product codes, but may omit unused codes or codes designating products for which no information is to be made available.

The IP-address field in each row of the cross-reference table 215 holds a 32-bit IP address used to route Internet data packets to a destination computer using the TCP/IP protocol. The 32-bit IP address value in the cross-reference table 215 is obtained from the IP address field of the URL table 213, and that 32-bit address value is prefetched by querying a conventional domain name server (DNS) seen at 217 assigned to the cross-reference resource 101. The DNS 217 translates the alphanumeric URL in the URL field of the URL table 213 into the current 32-bit IP address used by Internet routers to guide data packets to the proper destination computer. The alphanumeric URL in the URL field of the URL table 213 is supplied via the registration template 207 when Internet location of the manufacturer's product description data is supplied during the registration process.

The separate URL table 213 has a one-to-many relationship to the cross-reference table 215 and uses the 32-bit IP address value as the relational key. This arrangement allows a single URL base address to be shared by a plurality of different manufacturers. Thus, for example, a single Internet service provider (ISP) may act as a shared Internet resource for storing data about a products originating from many different manufacturers. It is accordingly unnecessary for each manufacturer to operate its own server or have its own assigned URL. Instead, a manufacturer may place its product descriptions on any server having an assigned Internet address. Note that it is further unnecessary for the manufacturer to have, or supply, an assigned URL rather than a numerical IP address; however, since corresponding URL's are ordinarily available and easier to remember, and because it may be desirable to later change numerical IP addresses while retaining the same URL, the use of URL's for registration is preferred.

Note also that, because URL/IP address assignments may be added, altered or deleted on a daily basis by the URL assignment authority, updates to the DNS tables should also be reflected by automatic updates to the cross-reference table IP-Address fields. In this way, a change in URL/IP address assignments propagated in the DNS system require no additional action on behalf of the manufacturers to insure the continuing ability of the product code translator to produce the appropriate new IP addresses in response to universal product code queries. If, as discussed later, the Internet domain name system itself is used as the product code to IP address translation mechanism, updating two tables would be unnecessary.

With the foregoing as background, the registration and query/response functions performed by the product code translator may by summarized as follows: each participating manufacturer, or someone acting on its behalf, submits a registration which generates an incoming registration template 207 containing information about the registering manufacturer, including an identification of the universal product codes which designate products for which information is to be made available, together with the URL which specifies the Internet resource which will make that product information available.

The supplied URL is stored in the URL Table 213 and converted into a numerical IP address in the IPAdr field of the URL Table 213 using an available domain name server 217. This 32 bit IP address is stored in the IPAdr field of the cross-reference record (row) in table 215, along with a specification of the universal product codes of the products described by information which is available at this IP address, the range of codes being specified by the values stored in the FromCode and ThruCode fields in the new record in cross-reference table 215.

When an incoming query is received by the query handler 204, a table lookup function is performed by searching the cross-reference table 215 for a row record or records which specify a set of universal product codes which include the code or codes specified by the query. If matching row(s) are found, the IP-address(es) found in the matching row(s) are returned to the query submitter; otherwise, a special code (such as a zero valued IP Address) is returned to indicate that information for the product code(s) of interest has not been registered.

The Internet resource which acts as the product code translator can additionally perform some or all of the following additional functions:

It can respond to a request for information about a particular participating manufacturer and return to the requester the information in the company table 211 as well as the specification of all of the registered universal product codes assigned to that participating manufacturer and the IP address (or URL) of the location where further information on the products designated by the registered universal product codes may be obtained.

The product code translator can respond to a query containing a designation of one or more universal product codes by identifying the email address of the manufacturer. The product code translator, or any other computer which obtains cross-references between universal product codes and email addresses from the product code translator, may act as an SMTP forwarding agent; for example, forwarding email which contains a designation of universal product code from a sender to an email address designated by the manufacturer of the product designated by that code. Alternatively, resellers and others may obtain email addresses from the product code translator which can be included in "mailto:" hypertext links in product listings, allowing a webpage viewer to display and complete a blank email request for information which is routed directly to the manufacturer's designated email address. The email address returned in response to a request may be a standard email address such as "upcinfo@domainname" where "domainname" is the domain name portion of the URL supplied by the manufacturer, in which case the specific universal product code would, by convention, be supplied as all or part of the "subject" of the email message sent to that address, enabling the manufacturer to identify the specific product which is the subject of the inquiry.

The product code translator can further provide all or part of the information from company table 211 to provide information about the manufacturer(s) to whom registered universal product code or codes are assigned. Note that, in general, the information which is required or recommended for inclusion with other company information may be limited to that data necessary or desirable to enable the code translator to perform its functions. Other information about the company may simply be placed in an allocated namespace on the manufacturer's server.

The cross-referencing utility can provide the entire contents of its URL table to a requesting computer, such as a search engine which can then perform conventional "web crawler" indexing of the websites specified by the listed URLs and/or IP addresses, thereby generating complete or partial indexes to all or less than all of the products whose product description locations have been registered with the product code translator.

The cross-reference table 215 can be scanned by the product code translator in response to a request for certain universal product codes only; for example, books are assigned EAN numbers which always begin with the prefix number 978 before the company-id value (publisher designation) portion of the International Standard Book Number (ISBN) which makes up the remainder of the EAN number for each book, allowing all IP addresses for information about books to be provided by the cross-referencing server to create a database or index to book information. In the same way, the cross-reference table could be scanned for product codes assigned to a particular manufacturers (e.g. book publishers) to provide a more focused index.

The product code translator, as noted earlier, may facilitate the registration process by providing a website from which HTML registration form pages may be fetched, displayed and completed using a conventional web-browser program. In addition, the product code translator may advantageously make query forms available to permit information request queries to be made directly, as well presenting informational web pages which provide instructions and guidelines for registration procedures, recommendations for the storage of information on registered information resources, and instructions and downloadable software which may be used to simplify and facilitate searches and functions performed at other resources on the Internet which utilize the services provided by the product code translator. When, as discussed later, the Internet Domain Name System is employed to perform product code or company code translation to an Internet address, the authorized DNS registration authorities can provide informational and registration services to registrants.

Information Publication by Manufacturers

The present invention provides significant advantages and opportunities to manufacturers. Information which manufactures now distribute in other ways can be made immediately available to those who need or desire that information. Examples include text and graphics which describe and promote the sale of each product to potential buyers; product labeling information, some of which may be required to be made available to potential buyers such as product weights and volumes, ingredients, nutritional facts, dosage and use instructions, some or all of which is now included on product packaging and which can be reproduced as mixed text and graphics HTML page for viewing by distributors, retailers, advertisers, catalog publishers, potential customers and purchasers; logos, photographs of products, and other graphics files in a variety of resolutions for use by both electronic and print rendering to promote product sales, usage and support. Instructional and service information including self-help diagnostics and recommended solutions, product part lists and ordering information, product return procedures, current pricing information, identification of dealers and distributors, warranty and guarantee explanations, and support telephone numbers may be provided.

The scope and content of the information each manufacturer makes available is completely under the control of that manufacturer. In order to make this information accessible in a standard way, it is desirable that the manufacturer conform to standard resource naming conventions so that interested parties which obtain the manufacturer's registered IP address from the product code translator can find the desired information at this address. This naming convention may take numerous forms, and the following are merely exemplary:

A root directory named "upcinfo" may be created on each registered computer, and a subdirectory having a name which is the universal product code (expressed as a zero-filled, right-justified fourteen digit number) is created to hold the information concerning the product designated by that universal product code. At the minimum, each such directory includes a product home page named "info.html" which typically provides whatever general product information the manufacturer wishes to place before all interested parties. This product home page may link to additional information related to the product on other pages when appropriate.

By way of example, a product HTML home page for a book would be created by the book's publisher and could include a complete bibliographic citation identifying the title, author, book type (hardcover, paperback, etc.), recommended retail price, ISBN number, number of pages, publication year, etc. In addition, each book's home page might include an imbedded thumbnail image (JPEG or GIF file) of the book jacket, and links could be added enabling the viewer to see additional information concerning that book when available, such as an interview with the book's author, quotes from favorable reviews, book group discussion guides, a table of contents or introductory chapter, etc.

Thus, information uniquely formatted to best advantage by the manufacturer could be made available by accessing a single URL, having the same form for all products, formed by combining the IP-address obtained from the standard by concatenating a prefix and suffix.

The suffix has the form:
"/upcinfo/12345678901234/info.html"

where the numerical part of the suffix is the universal product code directory name, and where the suffix is appended to the at the end of the prefix of the form:
"http://23.123.40.198"

consisting of the protocol identifier "http://" and by the 32-bit IP address from the product code translator written in its standard four decimal number format (four three digit numbers separated by periods, each of which is a value in the range 0–255 representing the binary value of one of the four 8-bit bytes making up the 32-bit IP address).

If a manufacturer stores product information in a database, the product directories and the HTML and other data files which are to be made available can be rewritten automatically under program control as the information in the manufacturer's database changes. Alternatively, a request for a particular "file," such as the web page designated "/upcinfo/product-code/info.html," may be intercepted at the manufacturer's server and handled as a database query to which the server responds by dynamically writing an HTML response page using information in the manufacturer's product database. Available database program development tools, such as Microsoft's Access 97 and Borland's Delphi 3.0, include database manipulation tools which allow programs to be readily written which automate the process of generating product description pages from an existing database.

The present invention may be employed to allow the same information found on a product's packaging to be made available to prospective online buyers. For food products, for example, in addition to the product name, logo and promotional materials, such existing packaging information typically includes an ingredient list, nutrition facts, serving suggestions and directions, recommended recipes, and product guarantee information. Over the counter pharmaceuticals, cosmetics and health care products often include further information, such as specific directions on dosage and use, warnings and instructions in the event of misuse, storage and product lifetime information, and active ingredient specifications. Frequently, this valuable information is printed on a product container or container insert which is discarded shortly after purchase. By making this information readily available to purchasers and end-users over the Internet, the manufacturer can help insure that such valuable product information, some of which may be legally required on the product's packaging, is available to the consumer at the time of an online sale and after the product has been purchased.

While information of the kind traditionally placed on product packaging already exists and can be converted by the manufacturer into a format suitable for publication on the World Wide Web, and thus made widely available at little cost, the invention allows information in other forms to be provided at low incremental cost. For example, multimedia presentations may be presented to promote, describe and support a product and its uses. User manuals and service documentation can be provided in Adobe Acrobat portable document format or the like for viewing and printing by resellers, service personnel and consumers.

It is frequently desirable to transfer to another computer data created by the manufacturer which provides limited product description information for each product offered to enable more efficient indexing, cataloging, inventory control, and other applications. By way of example, in the bookselling industry, publishers, distributors, retailers, and libraries often require a database of bibliographic information which consists, for each book, of the book title, author name(s), publisher's name, publication date, type of book (hardcover, paperback, etc.), page count, recommended retail price(s), and ISBN number (which takes the form of a subpart of the EAN universal product code). To the extent the content and format of data records which describe particular classes of products in particular industries and trade groups have been previously adopted and placed in widespread use, those structured data records may advantageously be made available utilizing the present invention. This is preferably achieved in two ways: a data record (file) containing such field-structured information about each product which is designated by a universal product code is placed by the manufacturer in the directory it creates for that product. This structured data record is given a filename indicative of the format used to store the structured data. For example, each directory bearing a name corresponding to the EAN number for a book would preferably contain a file named "biblio.dat" which contains a single structured record containing bibliographic data describing that book.

In addition, the manufacturer would place a combined file, also called "biblio.dat" in its root "\upcinfo" directory which contains all of the records for all of the products individually described in the subdirectories which have that structure in a single file. For most manufacturers, these structured data files, both individual record files in the subdirectories and the combined file in the root directory, may be automatically created and updated on a periodic or dynamic basis from the content of the manufacturer's existing database. The use of a single combined file at each server permits multi-manufacturer databases to be created by first retrieving the IP-addresses of all or part of the cross-reference table 215, and then retrieving and merging the combined data files from the "/upcinfo" directories from each identified server. Alternatively, when information about all of a given manufacturer's products of a given type is not desired, the needed individual structured data files can be retrieved from the individual product directories.

As described later in more detail, the information which the manufacturer makes available can advantageously be stored using the Extensible Markup Language (XML), which is also well suited for providing metadata which defines and describes the meaning of the various kinds of information that can be provided about individual products, groups of products, and the manufacturers and distributors from which those products are obtained.

This ability to obtain accurate and up-to-date product information from the manufacturer can substantially reduce the cost to resellers, catalog producers, and database vendors which is traditionally incurred in capturing this data by conventional means. For example, a retailer creating a computerized inventory control system for the first time with previously purchased merchandise may use a conventional hand-held barcode scanner to capture the universal product codes from all goods in inventory, and then retrieve complete and accurate product description records for each product via the Internet using the present invention.

The ability to obtain, update, and verify product description information by accessing manufacturer data can be readily included as callable functions built into inventory control and EDI software used by manufacturers, distributors, and retailers. Institutional "consumers," such as hospitals, government agencies, and libraries, may use the information to build internal databases for internal use.

The structured records noted above are typically, but not necessarily, copied into a separate database which is thereafter manipulated by the requester. Because each copied database record includes a field containing the universal product code, the ability to obtain and verify data in the remainder of the record from the manufacturer's server is retained. Note that it is possible for the user of the local database to verify, update and add to the product information specified by the universal product code at the time that data is referred to or relied upon. In addition, or in the alternative, the database can be periodically and automatically verified against current data made available by the manufacturer and updated to insure the continued completeness and accuracy of the entire local database.

The present invention enables a computer connected to the Internet to dynamically retrieve arbitrarily large quantities of data about an individual product when needed. This capability makes it unnecessary, and normally undesirable, to copy "content" into a local database which is not needed for structured indexing and retrieval purposes. Thus, again using books as example products, the local database might consist simply of title, author and publisher information to form a searchable local database. This database could be built by first obtaining all of the IP-addresses for universal product codes beginning with "978" (the EAN prefix for books) from the product code translator, retrieving the combined "biblio.dat" file from the "/upcinfo" directory at each IP-address, and extracting the universal product code, title, author and publisher data from these records to form the desired searchable local database. This database may then be rapidly searched to produce an output listing of all books meeting a specified search criteria, and complete information about each of the identified books can then be obtained using the universal product codes.

General product information indexes can be also readily be created by means of conventional "web crawler" indexing engines of the type now widely used to index World Wide Web sites. These indexing engines may scan either the product descriptions created by the manufacturer in the form of HTML or multimedia files, or the structured data files containing fielded information, or both. By limiting the scope of the information indexed to the product information data identified by the product code translator, search results produced by these product indexing systems are less likely to be obscured by references to other, less relevant information which happens to employ the term or terms used in a search request.

The principles of the invention may be applied to particular advantage by online resellers. By making detailed, accurate and up-to-date information about products which are offered readily available to interested prospective buyers, both the reseller and the manufacturer can more effectively promote the offered product to an interested buyer, and the buyer can make a more informed buying decision by obtaining more detailed information which facilitates product comparisons and matching the product's features with the buyer's needs.

In this regard, it may be noted that small retailers can employ shared software and services, and share access to product information and promotional materials made available by the manufacturer in accordance with the invention, at low costs, enabling even the smallest retailer to offer its entire inventory of products (and more) to its customers at low cost, with each product being fully described and promoted by the materials made available by the manufacturer. Similarly, small manufacturers can effectively describe and promote their products throughout a widespread distribution system by simply placing their available promotional and descriptive materials on an available shared server and registering the assigned universal product codes together with the shared server's address, for distribution by the product code translator, all at minimal cost.

In addition, the present invention may be used to advantage in combination with Electronic Data Interchange, a standard mechanism for exchanging business documents in standard format between computers. EDI systems typically use value added networks (VANs), such as the networks provided by GE, IBM Atlantis and Sterling, or EDI transfers can be made via the Internet using services such a those provided by EDI Network of Turnersville, N.J. Using EDI, manufacturers make available electronic catalog descriptions of their products being offered for distribution and resale. When a buyer selects products of interest to order from the vendor's catalog, the retailer's computer accesses the vendor's computer to transfer the U.P.C. codes to the retailer's computer without rekeying. The retailer may then issue an EDI 850 purchase order transaction which is sent to the vendor's mailbox. In addition, the EDI system may transfer limited additional information to the retailer, such as suggested retail price. When the products are shipped, an EDI 856 shipping notice is sent to the retailer containing bill of lading information (bill of lading number, carrier and weight), purchase order information, and carton contents using U.P.C. product codes and counts. The vendor also sends an EDI 810 invoice to the retailer in EDI format which enables the retailer to process the invoice and schedule payment either by check or electronic funds transfer, using an EDI 830 remittance advice transaction to give payment details for invoices being paid.

These EDI transactions enable retailers to not only automate product procurement functions but also to easily maintain an accurate inventory control system in which each product is designated by a universal product code. The present invention may be used to augment an EDI system by providing resellers and consumers with detailed product information and services for any product designated by a universal product code which is made by a participating manufacturer. As described later, a running application program such as an inventory control program may access supporting services from a manufacturer which relate to or support a given product by using the invention to convert the product code designating that product into the URI to which a Web service request is transmitted.

Internet Service Providers, such as the ISP indicated at 111 in FIG. 1, may provide shared computer services which interoperates with a reseller's inventory control system to provide customers with the information they desire before and after making purchases.

As seen in FIG. 1, and as previously discussed, a reseller (including both the example distributor 105 and the example retailer 107) may be assumed to have conventional inventory control systems, typically using EDI document processing, which includes in each case inventory data consisting of at least the universal product code for each product and, typically, count numbers indicating quantity on hand, quantity on order, quantity back-ordered, etc. This limited part of the reseller's database can be transferred from the reseller's inventory database (at 105 or 107) to an ISP 111 which serves many resellers but maintains a table of universal product codes for all goods offered by each reseller served, together with the on-hand counts for each code.

The ISP 111 hosts a website for each reseller served in conventional fashion, typically using a domain name assigned to the reseller. The ISP further makes available online merchant software which enables customers to search the reseller's website for products of interest, and view lists of products resulting from each search. Examples of such merchant software include Microsoft Site Server, available from Microsoft Corporation, and Merchantec Softcart marketed by Mercantec, Inc. of Lisle, Ill. Using the present invention, product listings presented to customers by these online merchant software systems may be enhanced with links to detailed information about any product of interest made available by participating manufacturers. The searchable product database used by the ISP 111 may be built, as described above, using the universal product codes supplied by the retailer to access the structured data files made available by the participating manufacturers (e.g, manufacturer 103 in FIG. 1) at the IP-addresses supplied by the product code translator.

The implementation of the invention may be facilitated by supporting software which performs a number of utility functions. As noted above, programs may be readily written to automate the conversion of information stored in a manufacturer's existing product database into the form of static or dynamically generated HTML pages which can be transmitted to fulfill information requests routed to the manufacturer by the cross-referencing facility. Industry and inter-industry groups can promulgate standards and guidelines which will promote consistent formats for product descriptions which are accessed in accordance with the invention. Inventory control and online merchant software can be readily enhanced to take advantage of the availability of database records and more robust product descriptions and supporting Web services which are made available via the Internet. Product information can be made available at terminals and kiosks placed in retail stores, showrooms and public places using conventional Web browsers which execute hypertext links to product information as well as other applications programs which may invoke product and company related Web services at product-code based URIs.

Using HTTP Relocation to Redirect Product Information Request Messages

The Perl program show.pl, listed in detail in the microfiche appendix, is a CGI (Common Gateway Interface) program which executes on a Web server and which operates as a product code translator as seen at 101 in FIG. 1. This illustrative program uses a file-based database rather than the relational database depicted in FIG. 2. The database consists of a set of files, each of which is designated by a file name consisting of a company code followed by the suffix ".xrl" and each containing cross-referencing information for all product codes beginning with that company code. The Perl program show is specially adapted to locate information on books which are generated by a universal product code known as the International Standard Book Number (ISBN), a nine digit decimal number followed by a check character, used by the publishing houses, book distributors, retail bookstores and libraries to uniquely identify books. A variable number of leading digits of each ISBN designate particular publishers, with the remaining digits being assigned by that publisher to designate a particular edition of a particular book.

The Perl program show.pl processes an incoming HTTP message containing a parameter which specified the value of a universal product code (in this case, an ISBN number), performs a table lookup operation to retrieve the URL at which information about the product specified by that URL may be found, and then returns an "error" message to the requesting browser which contains that URL in the response message's "Location" response field. As specified in Section 10.11 of the Hypertext Transfer Protocol—HTTP/1.0 specification, RFC 1945 (May 1996), the Location response-header field defines the exact location of the resource that was identified by the Request-URI. for type 3xx responses, and the location field must indicate the server's preferred URL for automatic redirection to the resource. Only one absolute URL is allowed. The response header may also include the status code 302 which, under the HTTP protocol, indicates that the target data has "moved temporarily" to the URL specified in the location field. In practice, however, it has been found that inclusion of a status code value is not necessary to enable existing web browser programs to automatically redirect the original request to the new location specified in the location response header.

The Perl CGI program processes an incoming HTTP message request directed to a URL of the form "http://www.upclink.com/cgi-bin/show?isbn=1234567890" which is parsed as follows: "www.upclink.com/cgi-bin" is the name of the directory holding the show.pl Perl program and "show?isbn=1234567890" calls the show.pl CGI program and passes to that program the parameter "1234567890" represented by the parameter name "isbn". The ability to execute Perl CGI programs is a common feature of most web servers, and is described, for example, in "Developing CGI Applications with Perl" by John Deep and Peter Holfelder, ISBN 0-471-14158-5 (John Wiley & Sons—1996). The Perl programming language is described in many texts including *"Perl 5 Complete"* by Edward S. Peschko and Michele DeWolfe, ISBN 0-07-913698-2 (McGraw Hill 1998). Hypertext Markup Language is also widely used and described, for example, in *"HTML Publishing Bible"* by Alan Simpson, ISBN 0-7645-3009-7 (IDG Books Worldwide 1996).

Figure 3:
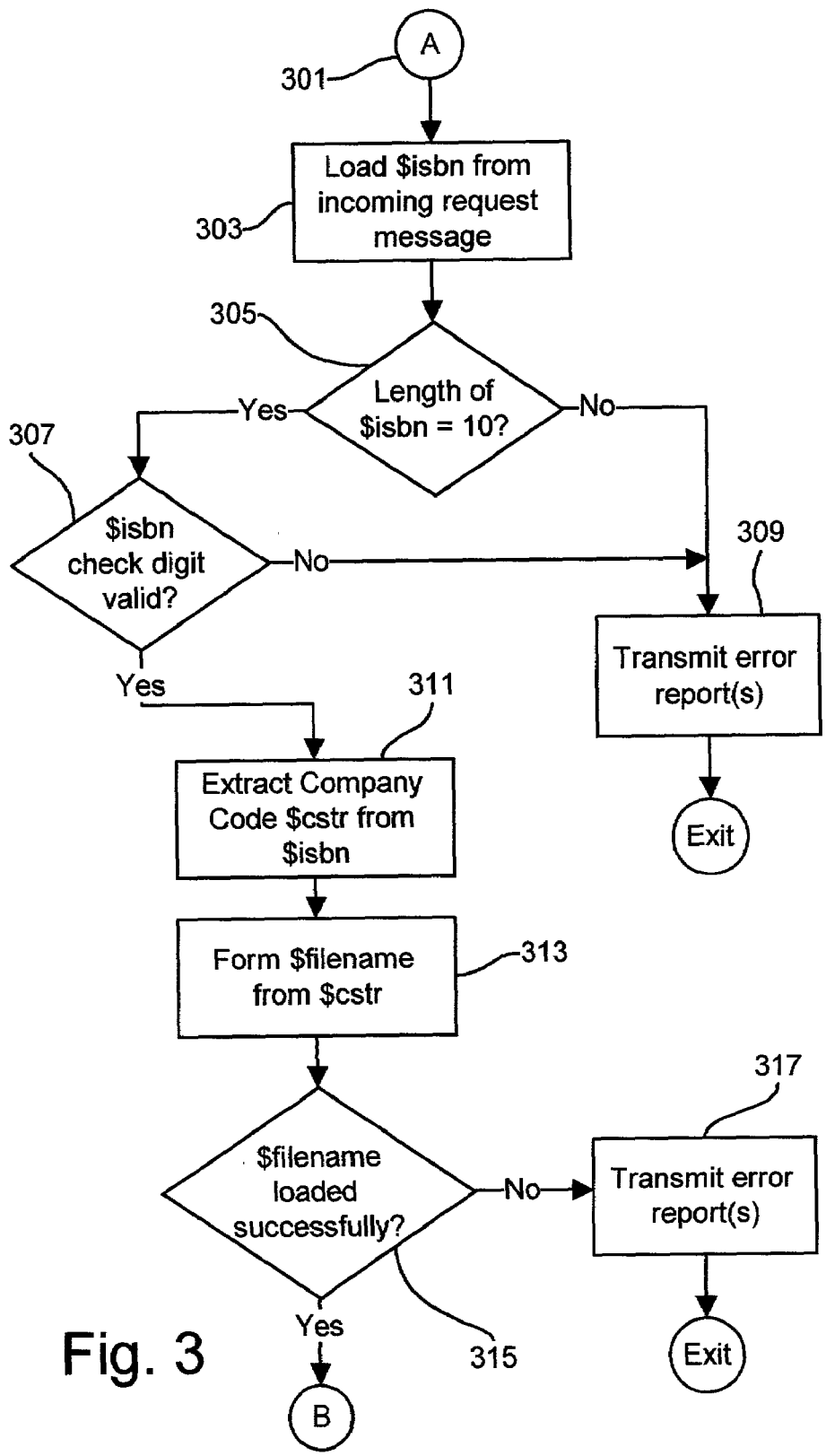
FIGS. 3 and 4 are a flow diagram depicting the operation of a CGI program which implements the product code translator, responding to request HTTP messages containing universal product codes and redirecting those request messages to the URLs where information about designated products may be found.

As seen in FIG. 3, the show program is entered at 301 and calls a sub routine named get_isbn which processes the incoming message. As indicated at 303, the subroutine get_isbn first loads the input string variable named $isbn with the parameter named "isbn" supplied by the calling message. The subroutine get_isbn then calls the subroutine isbn_message which returns the string "ok" if the contents of $isbn satisfy the requirements for a correct ISBN (International Standard Book Number); that is, the string must contain 10 digits as indicated by the test at 305 and, as indicated as 307, the first nine digits must translate using a predetermined algorithm (performed by the subroutine check_char) into a check digit character which matches the last (10 th) character in the incoming ISBN number stored as the string $isbn.

The algorithm for generating an ISBN check characters works as follows. First, note that an EAN numbers for books may be converted to the book's ISBN number by removing the first three digits (978) and the last digit from the EAN (the last digit is the EAN check digit, leaving a nine-digit number. For example, EAN 9780940016330 becomes ISBN 094001633 (the first nine digits without the ISBN check character. To generate the ISBN check character, each ISBN digit is multiplied by a predetermined associated weighting factor and the resulting products are added together. The weighting factors for the first nine digits begin with 10 and form the descending series 10, 9, 8 . . . 2. Thus for the nine digits 0 9 4 0 0 1 6 3 3, the products summed are 0+81+32+0+0+5+24+9+6=157. This sum is divided by the number 11. ($157/11$=14 with 3 remainder). The remainder, if any, is subtracted from 11 to get the check digit. (11−3=8). If the check digit is 10, it is represented by the Roman numeral X. The final ISBN in our example is accordingly 0-940016-33-8. By generating the check digit and comparing it with the received check digit, the validity of the ISBN may be verified.

If the incoming ISBN string passes all of these tests, the routine isbn_message returns "ok," otherwise, it returns an appropriate error message and the subroutine send_error_page is called at 309 to write and transmit an HTML error page to the requester, advising that the ISBN number supplied was incorrect.

When the request containing an invalid ISBN number is being supplied from a source other than the user, such as an online retailer's web site which employs the ISBN number supplied by its inventory control system, an advisory error message can also be sent directly to the retailer to indicate that an error was detected. Although such an advisory should be unnecessary, since a similar algorithm for identifying invalid ISBN numbers should be used by the retailer to validate the data before transmission, it is nonetheless desirable to report such errors to the source as well. The error report may sent as an accumulated error log file or as an immediately transmitted message sent to a predetermined error message handling routine provided at the retailer's server.

If the $isbn variable meets the length and check-digit tests, it is processed by the subroutine make_cocode which determines, for that ISBN number, how many of the leading digits constitute the "company code" which is assigned to a particular publisher. The routine make_cocode performs this operation by calling the subroutine second_hyphen_position which performs tests to determine the number of digits in the company code which can be established from the value of $isbn.

The relationship between any given ISBN and the URL which identifies the source of information about the book designated by the ISBN is selected by the party (typically the publisher or its designated agent) which controls the server which provides that information. Because different publishers and their web site hosts may use different methods for establishing URLs for their book information, the Perl script show.pl operates in different ways depending on the company code $cc which forms the leading digits of the incoming ISBN.

The show.pl script handles these differences by fetching a file of control information from a file having the name "../link/cocode.xrl" which is constructed from the company code. The portion "../link/" is a predetermined data directory available to the CGI script show.pl, "cocode" is the numerical string corresponding to the company code extracted at 311 from the ISBN by the make_cocode routine, and ".xrl" is a standard file suffix. For example, if the incoming ISBN is "8870812345" the routine make_cocode will determine that the first five digits are the company code, causing file name"../link/88708.xrl" to be stored as the variable $cstr. As seen at 313 in FIG. 1, the subroutine load_xrl loads the named control file from local disk space at the cross-referencing server which executes the Perl script. If the file named $cstr is not found, an error report is issued indicating that no cross-referencing data has been supplied by the company identified by the company code in $cstr as seen at 315 and 317.

Figure 4:
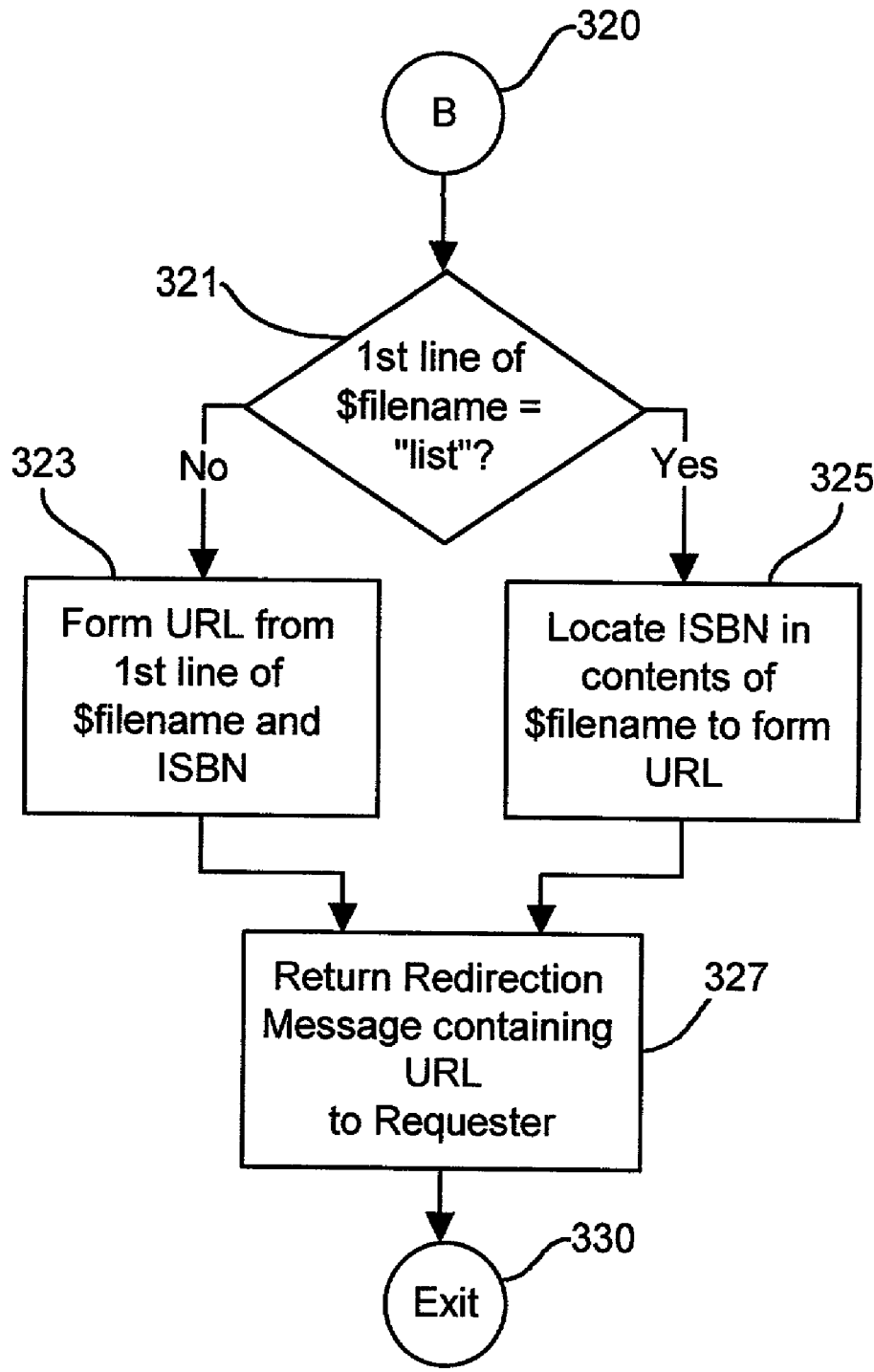

The contents of the fetched file are then analyzed by load_xrl which fetches the first line and performs a test at 321 (in FIG. 4) to determine if the fetched file is a multiline text file with the first line holding the string "list". If not, the file contains a single line.

If the file is a single line file, as seen at 323, the contents of the single line are used in combination with the ISBN number to form the URL which specifies where the desired book information may be obtained. For example, if the first line of the control file named "../link/88708.xrl" contains the string "hstp://www.upclink.com/ss/ .html", the subroutine load_xrl inserts the hyphenated form of the ISBN at the position indicated by the space to form the URL "http://www.upclink.com/ss/88708-1234-5.html". The first and second characters of the control file are used to identify variations in the manner in which the ISBN and the control file string are combined to form the URL. For example, if second character of the control file (an "s" in the example) is an "s", the ISBN is hyphenated before being substituted for the space in the string, and the "s" is replaced with a "t".

If the first line of a multiline control file contains the string "list", all of the lines of the control file are read into a hash table. Each line contains both an ISBN and the URL where information about the book identified by that ISBN can be found. A hash table lookup is then performed to find the particular line holding the target ISBN, and the desired URL is obtained from the line found as indicated at 325 in FIG. 4.

After the target URL is formed, the subroutine send_response returns an HTTP response message to the requesting browser which reads:

"Content-type: text/html\n location: $target \n\n" where the URL previously determined is substituted where $target appears. This message is interpreted by the web browser which receives the message as an indication that the requested information (requested from the URL "http://www.upclink.com/cgi-bin/show$isbn=1234567890") has been relocated to the URL specified by $target. The requesting web browser then automatically resends the request to the location where the needed information is actually located, and does so in a way that is transparent to the user who will normally be unaware that the transmitted request has been redirected to a different location.

Figure 5:
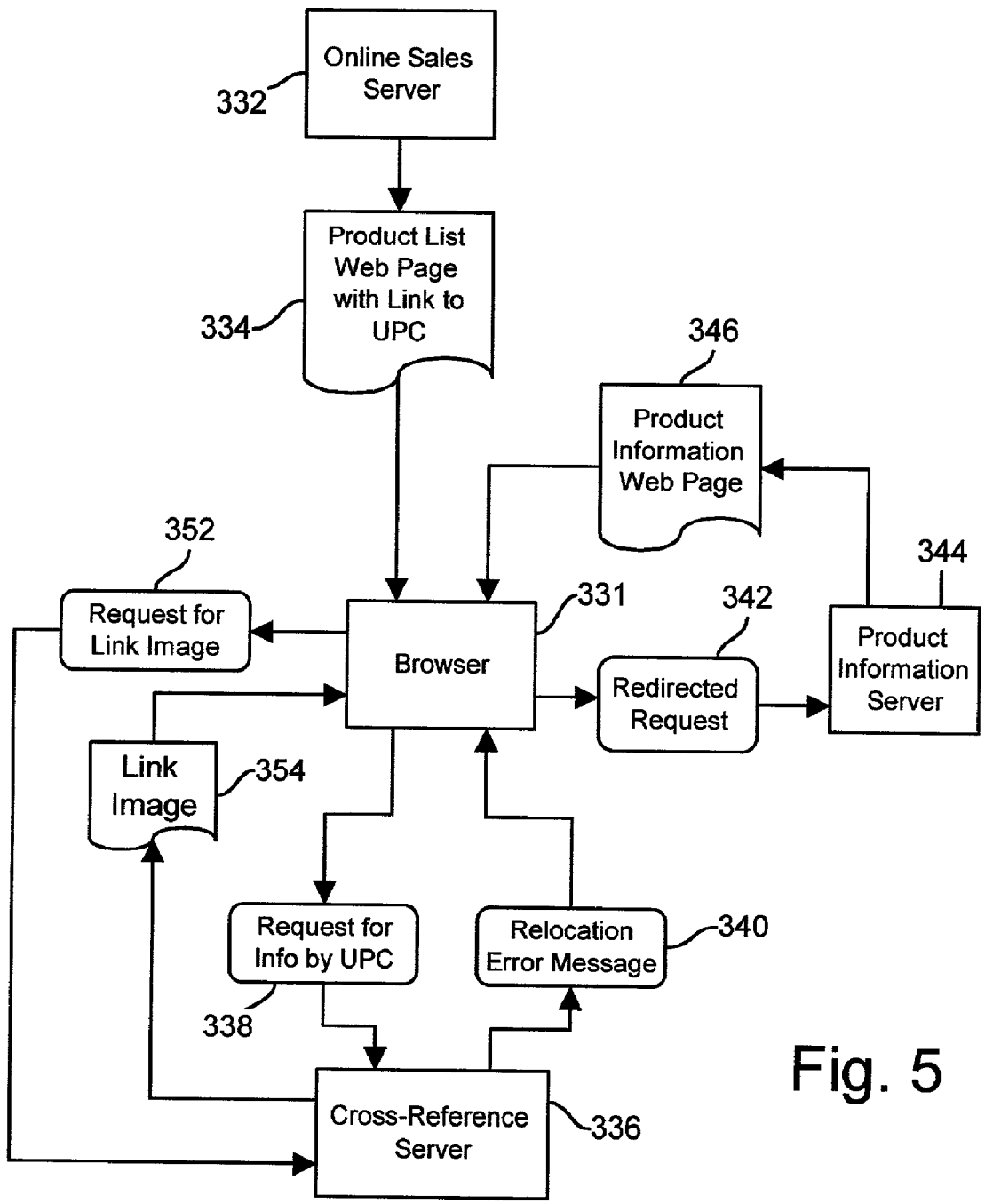
FIG. 5 is a data flow diagram illustrating the manner in which a web browser interacts with a server which acts as a product code translator by redirecting links on a merchant's web page to product information made available by the manufacturer.

FIG. 5 of the drawings provides an overview of the typical operation of the CGI Perl script show.pl described above. An online shopper manipulates a web browser application program indicated at 330 to look for and purchase a particular book. In doing so, the shopper provides the browser 330 with the URL of an online book retailer which operates the online sales server seen at 332 in FIG. 5. During the browsing session, the sales server transmits a web page 334 which lists the citations to one or more books, and each of those citations anchors a hyperlink to the cross-reference server seen at 336.

The operator of the sales server which creates the book list web page needs nothing other than the ISBN number of the book to create a link. However, as part of its inventory control system database, the retail web site typically has limited additional information, such as the title, author name(s), publisher name, as well as the ISBN. Using this available information, the book listing webpage can include an informative citation to the book which forms the anchor of a hyperlink to additional information. For example, if the following citation information from the retailer's inventory control system is used to display the following book listing:

8 *Ball Chicks: A Year in the Violent World of Girl Gangs,* By Gini Sikes, Anchor Paperback, ISBN: 0-385-47432-6. Learn More The hyperlink anchor "Learn More" at the end of the citation is formed by the following HTML:

<a href={URL}>Learn More </a> where {URL} is a URL such as:
"http://www.upclink.com/cgi-bin/show-?isbn=0553571656"

When the anchor text "Learn More" on the web page 334 is clicked on by the shopper, an HTTP request message 338 is sent to the href address of the cross-referencing server 336, triggering the execution of the CGI Perl program show.pl which returns the redirection error message 340, thereby informing the web-browser 330 that the desired information is at a different location. The web browser 330 immediately (and transparently to the shopper) reissues the request to the address specified in the relocation error message. This redirected request, seen at 342, is transmitted to the product information server 344 operated by the publisher, which returns a web page 346 to the browser containing the desired additional information on the book. The web page 346 typically includes an image of the book jacket, a synopsis of the book, and brief reviews, and may well contain links to additional information provided by the publisher, such as an author interview, a table of contents, or whatever else the publisher may wish to include. In this way, the buyer is provided with up-to-date and detailed book information which is equivalent to or superior to the information which may be obtained by picking up the book from the shelf of a "bricks-and-mortar" bookstore.

Image-Cued Links

Because additional information may not be available via the Internet from the publisher for all of the books in the retailer's inventory, it is desirable to provide a mechanism which avoids suggesting that a site visitor should click on links that will ultimately prove unworkable.

The mechanism involves the prior retrieval of data describing which universal product codes have been registered before web pages containing links using these codes are generated. For example, a sales website could transmit a list of the company codes for those universal product codes of products to be offered for sale, and obtain in return a listing of those company codes which have been registered. Alternatively, a list of supported company codes could be periodically broadcast (e.g. by FTP transmission) to subscribers. The sales website could then use this list to distinguish those products for which additional information was being made available by the manufacturer from those for which there is no additional information, and include links on product lists only when they will work.

Alternatively, the web page producing site can perform a prior fetch of the needed Internet addresses from which product information may be obtained by sending a request message containing one or more universal product codes (or company codes) to the cross-referencing server and receive in return a list of the corresponding Internet addresses. In this way, the links to additional information contained on product list pages can be refer to the manufacturer's servers directly, and can suppress the creation of links when no information has been made available.

A mechanism here called "Image-cued links" can also be used to suppress the appearance on a web page of links to unavailable product or company information. For example, an image-cued link can display a graphical icon for a book listing on web page 334 which might be either a visible button with the legend "Learn More" or an invisible (transparent or single-pixel) graphic image, depending on whether or not the ISBN for a listed book has a corresponding URL stored at the cross-referencing server 336. The HTML for an image-cued link to information about the book identified by ISBN 0821219804 might be written like this:

<a href={url-1}><img src={url-1} border="0"width="51" height="21"> where {url-1} is a URL such as:
    "http://www.upclink.com/cgi-bin/show-?isbn=0821219804" and where {url2} is a URL such as:
    "http://www.upclink.com/cgi-bin/button-?isbn=0821219804"

where the "anchor" for the link to the CGI script named "show" is an imbedded image (fetched from a different CGI script named "button" which also executes on the cross-reference server). The Perl script button.pl is also reproduced in the Appendix and performs the same initial processing of the incoming ISBN number as the script show.pl. Both show.pl and button.pl determine whether data is available from which a cross-reference from an incoming ISBN number to a URL can be made. If it the cross-reference can be made, show.pl returns a relocation message containing the needed URL whereas button.pl returns the URL of an image that indicates that more information is available. If the cross-reference cannot be made, show.pl returns an error message in the form of an HTML page while button.pl returns the URL of a null image (either a transparent image or a single pixel image). Note that the content of the image file may be controlled by the web page producer since the CGI routine at the cross-referencing server (e.g. button.pl) may be unique to the caller and may hence return image URL's specified by the caller. Alternatively, a single CGI button routine can be used with the desired image URLs being passed as parameters to the cross-referencing server.

The net effect on the web page is the appearance of a button or other image inviting the site visitor to click on a link to learn more when more information is available, but to suppress the display of the button, or to display a "no information available" button or image when the cross-reference cannot be made. In this way, the site visitor is affirmatively informed when more information is available, and discouraged from looking further when no information is available, while the HTML placed on the book listing has a standard form which can be included without prior knowledge of whether needed data is available or not.

Product Code Cross-Referencing Using the Lightweight Directory Access Protocol

The Internet LDAP protocol may be used to advantage to implement the product code translation process. This protocol, developed at the University of Michigan and later further developed by Netscape Communications Corp. provides both access and update capabilities, allowing directory information to be created and managed as well as queried. LDAP is an open Internet standard, produced by the Internet Engineering Task Force (IETF), the same body responsible for creating TCP/IP, the Internet Domain Name System (DNS), and the hypertext transport protocol (HTTP). The LDAP protocol is defined in RFCs 1777 and 1778 and informational documentation is further provided in RFC 1823. The use of LDAP to provide directory lookup services via the Internet is further detailed in the literature. See, for example, *Implementing LDAP* by Mark Wilcox (Wrox Press—1999) and *LDAP—Programming Directory Enabled Applications with Lightweight Directory Access Protocol* by Tim Howes and Mark Smith ( Macmillan Technology Series—1997). Operational LDAP server software may be purchased from a variety of sources, and includes the "Netscape Directory Server" marketed by the Netscape Communications Corporation.

An LDAP server may be advantageously employed to store "entries," each of which is uniquely identified by a distinguished name (DN) which may take the form of the company code portion of the universal product code, creating a "flat namespace" in a single level tree structure, with the remainder of the entry including a string specifying the URL of the server resource from which information about products assigned that company code may be found. In one arrangement, an online merchant's server may send a request to a remote directory server using the LDAP protocol to obtain the URL at which information about a specific product is available. Next, the merchant's server could again use the LDAP protocol to fetch information about a specific product designated by the remainder of the universal product code from a second LDAP directory server at the URL specified by the first server, the second LDAP server being operated by the product manufacturer to store the URL at which data describing particular products is stored. The actual product data may advantageously be stored as XML "documents" as discussed later.

Product Code Cross-Referencing with Domain Name Servers

Cross-referencing a universal product code to the Internet address of the source of information about the product designated by that code can be advantageously performed by Internet domain name servers (DNS). Conventional Internet domain names are symbolic names (a character string) that identify different computers and resources on the Internet. While computers connected to the Internet actually use binary IP (Internet Protocol) addresses to find each other, people find words and abbreviations to be much more convenient to remember and use. The Internet domain name system assigns computers and resources a domain name that corresponds to the numerical IP address used to access that computer or resource. Each domain name must be unique, and server operators register their desired domain names with a domain name registration server which then provides the cross-references to the appropriate DNS name servers. The Internet domain name system that is currently in widespread use is described in RFCs 1034 and 1035. RFC 1034 provides an introduction to the Domain Name System (DNS), and omits many details which can be found in its companion RFC 1035 which is entitled "Domain Names—Implementation and Specification."

Domain names are composed of a hierarchy of names that appear in descending levels from right to left. Therefore, the levels that appear at the end of URLs and E-mail addresses are the first-level and second-level domains. For example, in the domain name "patentsoft.com," the suffix "com" is the first-level domain, and "patentsoft" is the second-level domain. By creating a new first-level domain (e.g. "upc"), the universal product code, or the company code portion of a set of universal product codes, could form the second-level domain. Alternatively, a preassigned name space may be reserved for product code to Internet address conversion by using universal product code or company prefix, perhaps combined with a distinguishing prefix, and an existing top level domain name. To achieve standardization, the full 14-digit GTIN number is preferably used as the second level domain name to create a registered domain name of the form:

12345678901234.info

Alternatively, a prefix or suffix might be combined with a product code or company code in the second level portion of the registered domain name as illustrated by the following examples:

upc123456789012.com
1234567890123ean.net
12345678901234.biz
cocode123456.com

Note that, if the company code portion universal product code is used as the second-level domain, as illustrated in the last example above, registration need only be done once for all product codes sharing that company code. Note also that, as noted earlier, it is desirable that each manufacturer respond to a request for information about that particular participating manufacturer. For example, retail merchants and distributors may advantageously use the company code portion of a universal product code to access a variety of useful information about the company generally, including contact information and distribution, shipping and discount policies. In this way, any retailer can use the web to obtain general information about a company while those retailers with established accounts with a particular vendor (as confirmed, for example, using digital signatures) may obtain private information which is hidden from the general public.

In this way, universal product codes and/or company codes can be used as domain names which are cross-referenced to IP addresses using existing DNS facilities. Thus, when a web browser issues a request directed to a URL including a company code domain name such as "123456.info," the DNS server (typically assigned by the customer's Internet service provider) responds with a corresponding IP address of an information server maintained by or for the company designated by the company code "123456" (assuming that company has registered the IP address corresponding to that company code based domain name with a DNS registration authority). If the assigned DNS server doesn't already have the cross-reference between a company code domain name (or a product code domain name) and the manufacturer's server's IP address, it asks the primary DNS server that is responsible for the domain if it has the server's IP address. If the primary DNS is busy or unavailable, it will ask the secondary DNS server assigned to that domain. When the customer's DNS server gets the manufacturer's server's IP address, it can then supply the destination IP address needed to transmit a request message to the manufacturer's server to access a designated resource relating to the identified company or product.

Note that product information can be obtained using a registered domain name that contains the company code only, with the remainder of the universal product code being passed in a further portion of the URI which designates the product information resource. For example, if "123456" is the company code portion of the product code "1234567890123," the full URI designating product information might take the form:

http://1232456.info/1234567890123/thumbnail.jpg which specifies a JPEG image file depicting a product identified by the EAN product code 1234567890123 which is available at a host identified by the domain name 123456.info. The manufacturer's server processes an HTTP request GET message containing this URI in the usual way to return the image file to the requester. The same result could be obtained by registering a domain name containing the full product code (e.g. "1234567890123.info") which cross references the same host server IP address. In this case, the HTTP request GET message would contain the URI:

http://12324567890123.info/1234567890123/thumbnail.jpg and would produce the same result. Each product code in active use by a single manufacturer might be associated with a company code domain name, and all such domain names would be cross referenced to the same IP address. The technique of cross-referencing multiple, different domain names to the same IP address is known as "name based virtual hosting" and permits a single server to support multiple domain names which are cross-referenced in the DNS name server to a single IP address. In this way, a manufacturer to whom multiple company codes have been assigned could support multiple company code domain names, and multiple product code domain names for each company code, using a single server and a single IP address.

Alternatively, a single server may use IP-based virtual hosting to support multiple domain names which the DNS name server cross-references to different IP addresses. IP-based virtual hosts use the IP address of the connection to determine the correct virtual host to serve and accordingly need to have a separate IP address for each host. With name-based virtual hosting, the server obtains the hostname which is supplied as part of the HTTP headers. Using this technique, many different hosts can share the same IP address. Name-based virtual hosting is usually simpler, and the administrator of the manufacturer's server need only configure the HTTP Server to recognize the different hostnames. The configuration file maps each designated domain name to a root directory in the server's mass storage system. Name-based virtual hosting also eases the demand for scarce IP addresses and would typically be used unless there is a specific reason to choose IP-based virtual hosting.

In the Internet Domain Name System, different domain names (such as a group of different product and company code based domain names) can be registered in the conventional way to refer to the same IP address. Section 3.6.2, Aliases and canonical names, of RFC 1034, DOMAIN NAMES—CONCEPTS AND FACILITIES, P. Mockapetris (November 1987), DNS also provides specific mechanisms which permit different domain names to be translated into the same IP address. One mechanism uses the canonical name (CNAME) resource record (RR). A CNAME RR identifies its owner name as an alias, and specifies the corresponding canonical name in the RDATA section of the RR. CNAME RRs cause special action in DNS software. When a name server fails to find a desired RR in the resource set associated with the domain name, it checks to see if the resource set consists of a CNAME record with a matching class. If so, the name server includes the CNAME record in the response and restarts the query at the domain name specified in the data field of the CNAME record. The one exception to this rule is that queries which match the CNAME type are not restarted.

For example, suppose a name server was processing a query with for 1234567890123.info and found the following resource records:

```
1234567890123.info  IN   CNAME PATENTSOFT.COM
PATENTSOFT.COM      IN   A     209.179.179.18
```

By using registering the product code based domain name 1234567890123. info as an alias of the canonical name PATENTSOFT.COM, a request for product information specifying the URI "http://1234567890123.info/" would be redirected by DNS to the IP address assigned to PATENTSOFT.COM.

As similar result occurs for domain names placed in pointer (PTR) resource records that always point at the primary name and not the alias. This avoids extra indirections in accessing information. For example, the PTR RR for the above host should be:

```
18.179.179.209.IN-ADDR.ARPA      IN      PTR
  1234567890123.info
```

Note also that different universal product code systems, such as the UPC codes used in the United States and Canada and the EAN codes used elsewhere in world have traditionally used a different number of digits in their product code systems. All of these coding systems have been subsumed into the a 14 decimal digit universal product code called the "Global Trade Item Number" or "GTIN" whose format permits any of the earlier codes to be represented in a standard 14 digit format. Thus, any of these existing universal product codes can be represented in a standard 14 digit format recommended for use in database applications and that can also advantageously form a standard format second-level portion of a domain name, with the first level domain (also called the top level domain or TLD) being any of existing first level domains, or a new top level domain not previously allocated. At the time the domain names containing a given company code and/or a given product code is registered with the Domain Name System, appropriate procedures may be used to confirm that the applicant for DNS registration has been assigned the right to use that particular code in the existing uniform product code system, or has authority to act on behalf of the true assignee of that code. In this way, the existing universal product code registration authority retains primary responsibility for assigning codes, whereas the DNS registrar at most need only confirm the identity of the DNS registrant.

The format and usage the preferred Global Trade Item Number (GTIN) is described in the *Global Trade Item Number Application Guideline* promulgated by the EAN—UCC System. A GTIN (Global Trade Item Number) is used for the unique identification of trade items worldwide within the EAN—UCC System. A GTIN has a fourteen-digit data structure though its data carrier (bar code) may contain only twelve digits (the U.P.C.), thirteen digits (EAN-13) or eight digits (EAN-8). The GTIN is defined as a 14-digit number to accommodate all the different structures. The term "trade item" refers to any product or service upon which there is a need to retrieve pre-defined information; this product or service may be priced, ordered, or invoiced at any point in the supply chain. This includes individual items as well as all of their different packaging configurations. There are four data structures for the GTIN; each provides unique numbers when right-justified in a 14-digit field:

UCC®-12 (Twelve Digits)
  Six digits representing the Company Prefix assigned by the UCC®
  Five digits representing the Item Reference Number
  One digit representing the Check Digit
  Or
  Eight digits representing the Company Prefix assigned by the UCC®
  Three digits representing the item Reference Number
  One digit representing the Check digit
EAN/UCC®-13 (Thirteen Digits)
  Twelve digits containing a variable length Company Prefix with the remaining portion of the twelve digits being the Item Reference Number
  One digit representing the Check Digit
EAN/UCC®-14 (Fourteen Digits)
  First Digit available to indicate packaging level Twelve digits containing a variable length Company Prefix with the remaining portion of the twelve digits being the Item Reference Number One digit representing the Check Digit EAN/UCC®-8 (Eight Digits)

Seven digits containing a variable length Company Prefix with the remainder of the seven digits being the Item Reference Number One digit representing the Check Digit If company codes rather than the full product code values are registered as part of the domain name, it is necessary for users who desire information or services relating to a product designated by a given universal product code to provide a mechanism for extracting the company code portion of from the product code in order to form the correct domain name. Although the company code for U.S. products is normally the first six digits of the UPC code, that is not true for many products (such as books originally designated by ISBN numbers and/or EAN numbers based on ISBN numbers, and products made abroad that bear EAN codes). Reliable extraction of a company code which takes these special cases into account requires a program-controlled process (see, by way of example, the discussion of the process 311 in FIG. 3 for extracting a company code from the product code for a book). Alternatively, a programmed process may first attempt to match the leading digits of a product code with a registered domain name by first testing the most likely six-digit combination to determine if it can be found in a DNS name server and, if that attempt fails, incrementally altering the number of leading digits extracted from the product code until a match is found or until it is determined that none of the permissible digits that might constitute a company code forms a match. By registering the complete product code as a part of registered domain name, this company code extraction process becomes unnecessary. In addition, the terminal digit in a complete product code is a check digit which should be retained in the domain name. The validity of a product code value which is included in a domain name that a manufacturer seeks to register may be verified by using the standard check digit algorithm at the time of registration.

Figure 6:
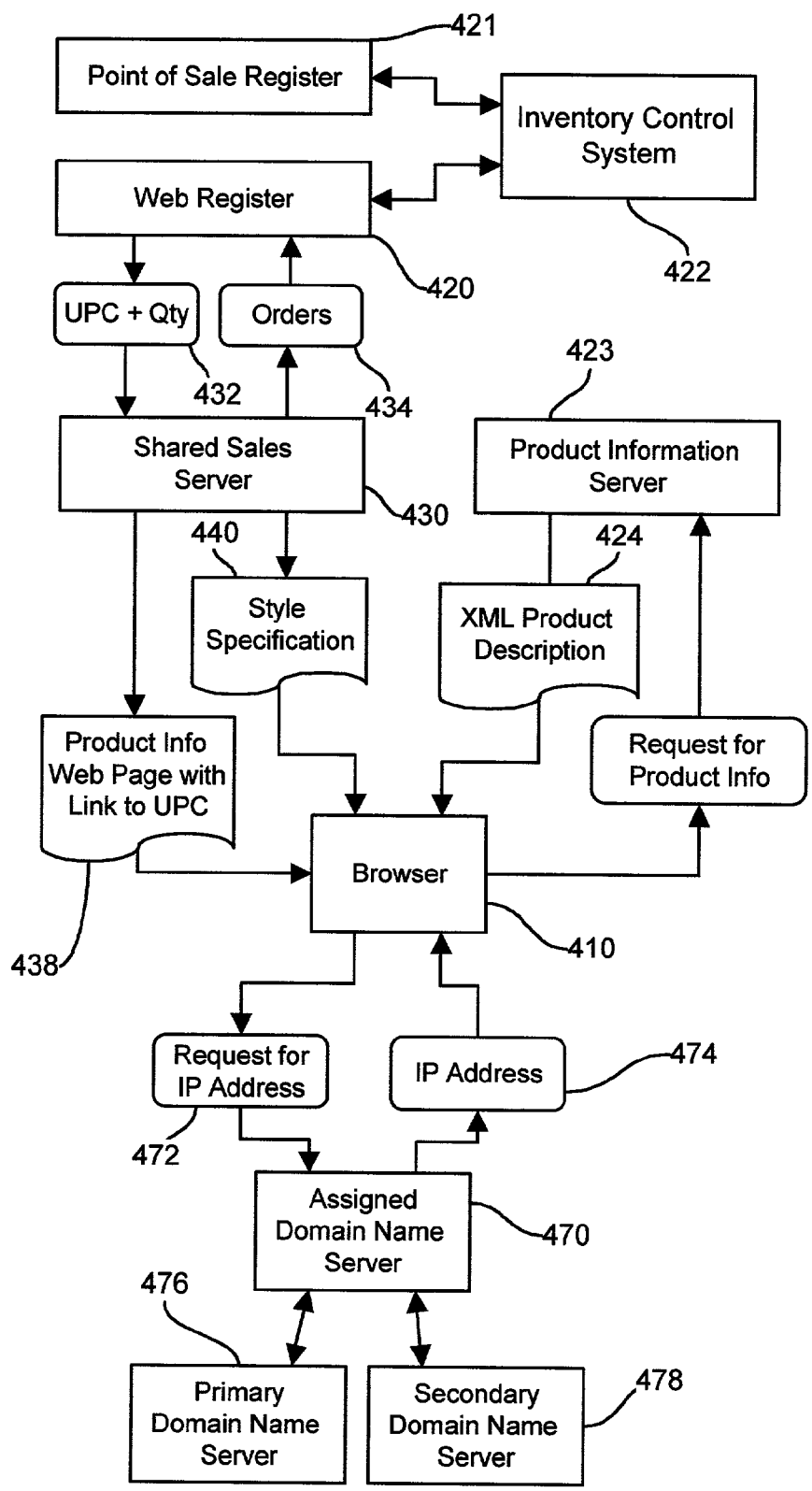
FIG. 6 is a data flow diagram illustrating a further embodiment of the invention in which a web browser interacts with a domain name server which serves as a product code translator, redirecting links on a merchant's web page to XML data provided by a shared sales server used by several merchants, the XML data from the manufacturer being displayed in accordance with an XSL stylesheet specification unique to each merchant, and the online merchant functions being implemented by the shared sales server which is connected to the conventional inventory control system operated by each of the merchants.

The use of the domain name server system as the mechanism for cross-referencing universal product codes and Internet addresses is used in the illustrative embodiment of the invention which is depicted in FIG. 6 and described next.

Using DNS, XML, XSL/CSS and XPointers

FIG. 6 of the drawings illustrates a system which permits computers operated by large numbers of manufacturers and large numbers of online retailers to work together to provide shopping services to customers via the World Wide Web.

FIG. 6 shows a browser 410 being used by an online shopper to view products offered by a retailer which operates an inventory control system computer seen at 422. The inventory control system 422 is conventional and includes one or more conventional point of sale registers as illustrated at 421 through which sales are made to customers who visit the physical "bricks and mortar" store. In addition, however, the inventory control system is provided with a "web register" which appears to the inventory control system to function in the same way as a conventional point of sale register but which, in fact, operates through a sales server 430 which provides Internet services on a shared basis to multiple retail stores and their inventory control systems. A communications pathway connects the web register 420 and the inventory control system 422 to the shared sales server 430, with the inventory control system 420 supplying the product codes and corresponding on-hand quantities as indicated at 432 and receiving from the shared sales server order information as indicated at 434.

A product information server 423 supplies product information to the browser 410 in the form of XML data as indicated at 424 in response to requests 425. The browser 410 preferably utilizes the Internet domain name system as proposed above to convert incoming universal product codes into Internet addresses, with the domain name system consisting of an assigned domain name server 470 which receives domain names containing universal product codes in address requests 472 and returns the registered Internet addresses 474 to the browser 410. When needed, the assigned domain name server 470 obtains the registered cross-references between domain names containing universal product codes and IP addresses from the primary DNS 476 or from the secondary DNS 478.

The shared sales server 430 sends web pages 438 containing information about products available from a connected retailer to the browser 410, along with XSL (Extensible Stylesheet Language) or CSS (Cascaded Style Sheets) style specifications as seen at 440. The use of XML and XSL or CSS provides several advantages. First, the selection and rendering of the product information is controlled by the links specified in the web page 438 as produced by the sales server. For example, if the web page 438 contains a product listing web page created in response to a search request from the browser 410, each included product description may include a link to only an that portion of an XML product description which contains a brief product description and a thumbnail image of the listed product, whereas, in response to a customer's request for more detailed information, the sales server may return a web page containing an XML "Xpointer" link to detailed product information and/or to an enlarged image of the product. In both cases, the style in which the XML data is rendered by the browser (e.g. typeface, font size and color, background color, etc.) is controlled by the style specification supplied by the sale server. In this way, the same XML data may have different visual styles when included on the pages created by different retail vendors.

The XSL (Extensible Stylesheet Language) consists of consists of two parts: (1) a language for transforming XML documents, and an XML vocabulary for specifying formatting semantics. An XSL stylesheet specifies the presentation of a class of XML documents by describing how an instance of the class is transformed into an XML document that uses the formatting vocabulary. XSL is described in the World Wide Web Consortium's "Extensible Stylesheet Language Specification," a working draft of which may be found at http://www.w3.org/TR/WD-xsl (Apr. 21, 1999). An XSL stylesheet processor accepts a document or data in XML and an XSL stylesheet and produces the presentation of that XML source content as intended by the stylesheet. It is contemplated that most major web browser applications will include XSL stylesheet processors which will enable them to convert the combination of XML and XSL data into a form, such as a viewable HTML web page, as specified by the XSL.

In addition to using XSL to specify the rendering style of XML data, cascaded style sheets (CSS) can also be used as set forth in the Proposed Recommendation dated Apr. 28, 1999 from the World Wide Web Consortium (see http://www.w3.org/TR/1999/xml-stylesheet-19990428). This specification allows a stylesheet to be associated with an XML document by including one or more processing instructions with a target of "xmi-stylesheet" in the document's prolog. The World Wide Web Consortium's recommendation regarding cascaded style sheets may be found at http://www.w3.org/TR/REC-CSS1(Jan. 11, 1999) which specifies level 1 of the Cascading Style Sheet mechanism (CSS1). CSS1 is a simple style sheet mechanism that allows authors and readers to attach style (e.g. fonts, colors and spacing) to HTML documents. The CSS1 language is human readable and writeable, and expresses style in common desktop publishing terminology. One of the fundamental features of CSS is that style sheets cascade; authors can attach a preferred style sheet, while the reader may have a personal style sheet to adjust for human or technological handicaps. Thus product descriptions as viewed on the browser may include content from the product manufacturer, reflect a preferred rendering style specification from the online reseller, as well as the personal style preferences of the viewer.

XSL could alternatively be used at the shared sales server 430 to transform XML data fetched by the server 430 from the manufacturer's server 423 and then converted into HTML documents with CSS style sheets at the sales server 430. This has the benefit of being backwards compatible with browsers which do not include the ability to handle XSL/CSS. Alternatively, XSL conversion can be performed on the server 430 to transform XML data into XML documents with CSS style sheets. XML, unlike HTML, comes with no formatting conventions and will always need a style sheet to be displayed. This method requires that the browser have the ability to use CSS to render XML. A third alternative is to use XSL to generate HTML/CSS on the client side, a method which requires that the browser have the ability to directly use CSS and XML, which older browsers cannot do. Finally, the browser may transform XML and XSL into "CSS formatting objects". Compared to the previous method, this method is more direct as the content isn't converted to/from HTML.

The ability to select only a portion of an XML product description document for reproduction on a web page is provided by the Xpointer protocol. As explained in the World Wide Web Consortium Working Draft of Mar. 3, 1998, at http://www.w3.org/TR/WD-xptr, the XML Pointer Language (Xpointer) document specifies a language that supports addressing into the internal structures of XML documents. In particular, it provides for specific reference to elements, character strings, and other parts of XML documents, whether or not they bear an explicit ID attribute. Using Xpointer, only selected portions of an XML product description made available from the manufacturer's server need be presented on a given web page, enabling the creator of the web page which links in XML data to control the nature and extent of the information shown.

The manner in which explicit relationships between two or more data objects, such as a retailer's product list page and the product information about a product listed on that page, may be expressed as a link asserted in elements contained in XML documents. These "XLinks" is the simplest case are like the HTML links described above in that they are expressed at one end of the link only, are initiated by users to initiate travel to the other end of the link, go only to one destination (which may be determined by a DNS server or by an independent cross-referencing server), and produce an effect which is mainly determined by the browser. The functionality of links is being vastly extended, however, by the XML Linking Language (XLink) specification being developed by the World Wide Web Consortium and available at http://www.w3.org/TR/WD-xlink. As extended, the XLink specification will provide more sophisticated multi-ended and typed links which can be used to advantage to automatically incorporate linked-in product information from one or more manufacturers into displays and multimedia presentations presented by retailers and others.

As previously discussed, in addition to the use of a product code translation utility which cross-references all or part of a universal product code into an Internet address, it is desirable to establish a protocol or convention which enables a requester to specific kinds of information about identified products or companies. In a conventional HTML system, this can be done by establishing naming conventions, as described above, for selectively locating different kinds of information about a product designated by a given universal product code, as well as different kinds of information about the company identified by the company code portion of the product code.

The metadata capabilities of XML can be used to advantage to provide an extensible system for dividing product and company information into a hierarchy of nested named elements which can be selectively accessed. Using the Document Type Descriptor (DTD) component of XML, the makeup of the required and optional components of such information can be defined in a standard way, facilitating the definition and validation of data structures to be used on various classes of products. Alternatively, the makeup of XML documents which contain product or company information may be specified in an XML Schema constructed in accordance with the World Wide Web Consortium's XML Schema Recommendation, parts 0, 1 and 2, issued on May 2, 2001.

The World Wide Web Consortium has further defined the "Resource Description Framework (RDF) and Syntax Specification" as described at http://www.w3.org/TR/REC-rdf-syntax. RDF provides a foundation for processing metadata (i.e. "data about data") and provides interoperability between computers that exchange information on the Web. Using RDF, data about products and companies, which can be accessed in accordance with the invention by using universal product codes; can be used by search engines to provide access to such information, can be used to automatically catalog the content and content relationships at particular web sites, pages or libraries; can be used by intelligent software agents to facilitate the sharing and exchange of information about companies and products. Using RDF with digital signatures, the privacy preferences and policies of the owners of product and company information can be selectively protected to help build the "Web of Trust" needed for electronic commerce.

Importantly, RDF provides a mechanism for defining metadata in a class system much like the class systems used by object oriented programming and modeling systems. Classes are organized in a hierarchy, with a collection of classes used for a particular purpose (such as the collection of classes describing a "product" and/or the collection of classes describing a "company") being called a "schema." RDF thus offers extensibility through subclass definition. For example, creating subclasses for a particular kinds of product (e.g., publications, software, foods, clothing, etc.) requires only incremental modification of a base "product" schema, and each such subclass may then be further modified to form descendant schema for even more particular kinds of product (e.g., magazines, video games, cereals, shirts, etc.). The shareability and extensibility of RDF also allows metadata authors to use multiple inheritance to mix definitions, providing multiple views of their data, and leveraging the work done by others. From a practical standpoint, the creation of a simple and generic product and company description base schemes which can thereafter be extending using RDF allows basic information about products and companies to be made available early, allowing more elaborate schemes to evolve as experience with the simpler system suggests their utility.

Using these techniques, the product manufacturer may be largely freed from concerns about web page design, formatting and integration with other information, and may concentrate on providing accurate and up-to-date text descriptions of its products, along with whatever images best describe the product, simply by registering the relationship between the manufacturers company code and/or universal product code(s) with the appropriate authority, and following the established content specifications for the information which the manufacturer makes available at the host specified by the registered product code or company code domain name.

It should be noted that XML, XSL, Xpointer, XLink and related Internet protocols and specifications are still being defined and extended, a process that can be expected to enhance the ability of the present invention to selectively and attractively provide information about products to those who desire that information from the most knowledgeable and reliable sources of that information.

The Shared Sales Server and the "Web Register"

Conventional retail stores display merchandise for purchase in physical showrooms for inspection and purchase by consumers. These stores typically obtain the products they sell from a large number of manufacturers, either directly or through distributors. Computerized inventory control systems are used to keep track of orders and sales in an effort to insure that goods are available for prompt delivery to customers when purchased while minimizing the expense of the maintaining an unsold inventory of products. Barcode checkout and EDI (Electronic Data Interchange) systems are commonly used in combination with inventory control systems to automate sales transactions. Customer checkout counters equipped with barcode readers automate the customer sales transaction, reducing errors and reducing costs. EDI, the computer-to-computer exchange of business documents in a standard format, automates transactions between the retailer and its suppliers by transferring sales documentation in electronic form, including the purchase order, the invoice, and the advance ship notice. Barcode readers and EDI services are now commonly used even by smaller retailers and have significantly reduced the cost of doing business.

In recent years, the Internet has produced new on-line sales mechanisms which promise to revolutionize retail sales. Using the World Wide Web, both manufacturers and resellers offer products to consumers for direct purchase with product delivery normally being accomplished by mail or a commercial delivery service. The consumer typically employs a web browser to search for products of interest and display product descriptions. Customers make purchases by completing one or more displayed forms to provide needed information (e.g. a credit card number and a shipping destination address).

Many successful web resellers take advantage of the fact that a web presence is inherently world-wide, and that the delivery charges of many services are largely independent of distance. Because a physical showroom is an unnecessary expense, web resellers can often successfully sell at much lower cost directly from one or more warehouses. To be successful, however, such a web reseller must make its presence known to a large audience. As a result, large and well-funded web resellers capable of effectively marketing on a nationwide scale have done well while those which have attempted to market their offerings locally or not at all have predictably been much less successful.

Large chain resellers with many retail outlets have also established successful web sales operations. Because the cost of creating and maintaining a web presence, as well as the cost of nationwide marketing, can effectively be shared among many retail outlets, and because much of the infrastructure needed to provide order fulfillment is already in place, such chain stores compete well with the nationwide web-only merchants.

Although customers would often benefit from the convenience of reviewing and ordering products from a local reseller, individual retail stores and smaller, local chains have typically been unable to justify the cost of creating and maintaining a web sales system. In addition to the substantial cost of installing and maintaining the needed hardware and software, the website owner must expend significant effort to create and periodically update the product descriptions which customers require in order to make informed purchases. The annual cost of operating a merchant website often far exceeds the revenue which the local merchant would derive from the limited probable volume of online sales.

The infrastructure depicted in FIG. 6 permits smaller and mid-sized merchants to profitably and efficiently offer online ordering services to their customers. By using the cross-referencing capability provided by the present invention, which provides customers with reliable product information direct from the manufacturer, and the shared sales server 430 and web register 420 which provides shareable functions which effectively connect the retailer's existing inventory control system 422 to the World Wide Web, the cost and complexity of retail web sales is largely eliminated, and the consumer obtains the convenience of shopping by computer with the other advantages of shopping with a local merchant.

The shared sales server 430 operates in the same way and provides the same functions as a conventional online merchant server: it enables customers to perform searches of available products and produces listings which the customer can review, with the ability to click on individual items to activate links to additional product information from the manufacturer's server as noted earlier. In addition, the shared server provides "shopping basket" and credit card transaction services to enable the customer to complete purchases.

The shared server 430 and the web register module 420 added to the retailer's existing inventory control system 322 maintain a connection via the Internet or a dial-up modem pathway which permits the inventory control system 422 to upload to the shared server 430 changes to the products (specified by universal product code) being offered for sale, and the quantity on hand. Each time any sale is made by any point of sale register 421 in the physical retail store or by the web register 422, the quantity on hand value associated with the sold product's code is altered. Similarly, when stock is replenished, the inventory control system 422 reflects the increased quantity on hand. The quantity on hand information passed as message information at 422 permits the shared sales server to maintain a database for each retailer served which indicates the products available for sale and the quantity on hand. When the quantity on hand equals or exceeds the quantity ordered, the on line order is accepted and passed at 434 from the shared server to the web register module 420 which posts the sale in the same way that a point of sale register posts a sale. The fact that the web register 420 performs the same functions as a conventional cash register enables the conventional inventory control system 422 to function in the normal way, with the exception that it must also update the product code and quantity on hand data maintained by the shared server. The fact that the shared server thus "knows" the inventory status allows the shared server to accurately inform the customer when shipment can be expected for goods on hand and when goods which must be replenished will be shipped with a delay. Orders sent to the inventory control system at 434 include the specification of products sold (by their universal product code designation) and the quantities of each sold, as well as address information for billing and shipping. Credit card transactions are handled on a shared basis using standard ecommerce software, either by sending encrypted credit card and other billing information to the retailer for handling, or actually performing the monetary transaction with the customer in its entirety on the shared server, and sending periodic payments and accounting records to the retailer.

Importantly, functions better performed by the retail store using resources best shared with the physical store's operations are not performed by the shared server 430 but rather by the store's inventory control system 422. Such functions include order fulfillment, inventory pricing, vendor ordering, reordering and payment, and warehouse management functions.

Examples of merchant server software which may be used to implement the shopping basket and credit card transactions performed by the shared server 403 include the Soft-Cart system offered by Mercantec, Inc. SoftCart 4.0 includes integration to the CyberCash system for credit card transactions and includes a Software Developer's Kit to enable a programmer to integrating SoftCart with WWW programs and legacy systems. A discussion of available Systems and techniques is found in *Designing Systems for Internet Commerce* By G. Winfield Treese and Lawrence C. Stewart ISBN: 0201571676 (Addison Wesley 1998).

In accordance with the invention, neither the shared server 430 nor the retail inventory control system 420 need store or maintain descriptive information about products. When an online customer desires information about a given product, it is obtained for review by the customer using XML Xpointer links to the manufacturer's server. XML information is located by supplying the universal product code for the product to the DNS server 472 which stores product code to Internet address conversion information. Product searches which locate products offered by a given retailer (as revealed by the product code and quantity on hand database) are displayed to the customer and, to the extent they result in purchases, are manifested by the transmission of a completed order to the retailer's inventory control system.

In a typical shopping transaction performed on the system shown in FIG. 6, a shopper employs the browser 410 to visit a web site which executes on the shared sales server 430. When the shopper reviews an HTML web page which lists available products, as illustrated at 438 in FIG. 6, the shopper can request additional information on any listed product by using the browser 410 to click on a link anchor on the page 438, thereby issuing are request 472 to the domain name server 470 for the IP address at which additional information on that product identified by a universal product code which forms part of the URL contained within the request 472. The DNS 470, consulting a primary DNS 476 or secondary DNS 478 if necessary, returns the IP address to the browser 410 which then issues a request 480 for XML product information to the product information server 422 maintained by the manufacturer of that product. Using the XSL stylesheet specification 440 supplied by the shared server 430 (in accordance with the background colors, font styles, etc. which may be characteristic for the web presence of the specific retailer), the browser presents the product description contained or specified by the XML data 424 to the user.

If the user decides to purchase the described product, the "shopping basket" functions of the shared sales server 430 are used to complete the order. Because the shared server 430 maintains a database for that retailer containing the quantity on hand values for each product offered by that server, the customer can be immediately informed if the shipment cannot be made whereas, if the product is available at the retailer's store or warehouse, the online customer's order can be confirmed for prompt delivery. When the order is completed by the shared server 430, the order 434 which includes the identification of the customer (name, shipping address, etc.) and the identification of the products sold (universal product codes plus quantities sold) is transmitted to the retailer's inventory control system 420. As explained in more detail below in connection with FIG. 7, the shared server 430 adjusts the quantity on hand values in its database, and the inventory control system 420 updates its database, with a cross check between the two being made if desired to insure consistency and synchronization.

It is important to observe that the arrangement shown in FIG. 6 isolates the retailer from substantially all of the concerns normally associated with the creation and maintenance of an online sales website. In accordance with the invention, the retailer need not be concerned with the creation or maintenance of accurate information on the products sold, since that task is appropriately born by the product manufacturer which has that information. Similarly, the retailer need not be concerned with the creation, hosting, and maintenance of a reliable and easy to use online shopping experience, a task performed by the shared server 430 for many different retailers. To the retailer, the shared server presents an interface to the inventory control system 420 which behaves much like conventional point-of-sale terminals (cash registers) indicated at 421.

This "web register" capability can advantageously be installed and maintained, with training being provided to the retailer, by inventory control system vendors as part of the normal inventory control system software, maintenance and training. The shared server functions can advantageously be made available by an independent Internet service provider (ISP) using standard e-commerce software, and the independent vendor of the shared sales server software can provide interface specifications and software support to the inventory control system vendors, enabling them to add the necessary "web register" interface functions to new or existing inventory control systems. In this way, each function is performed by an entity which is already experienced in that phase of the overall system requirements, and each function is provided at little additional cost over costs already born by each contributor.

Figure 7:
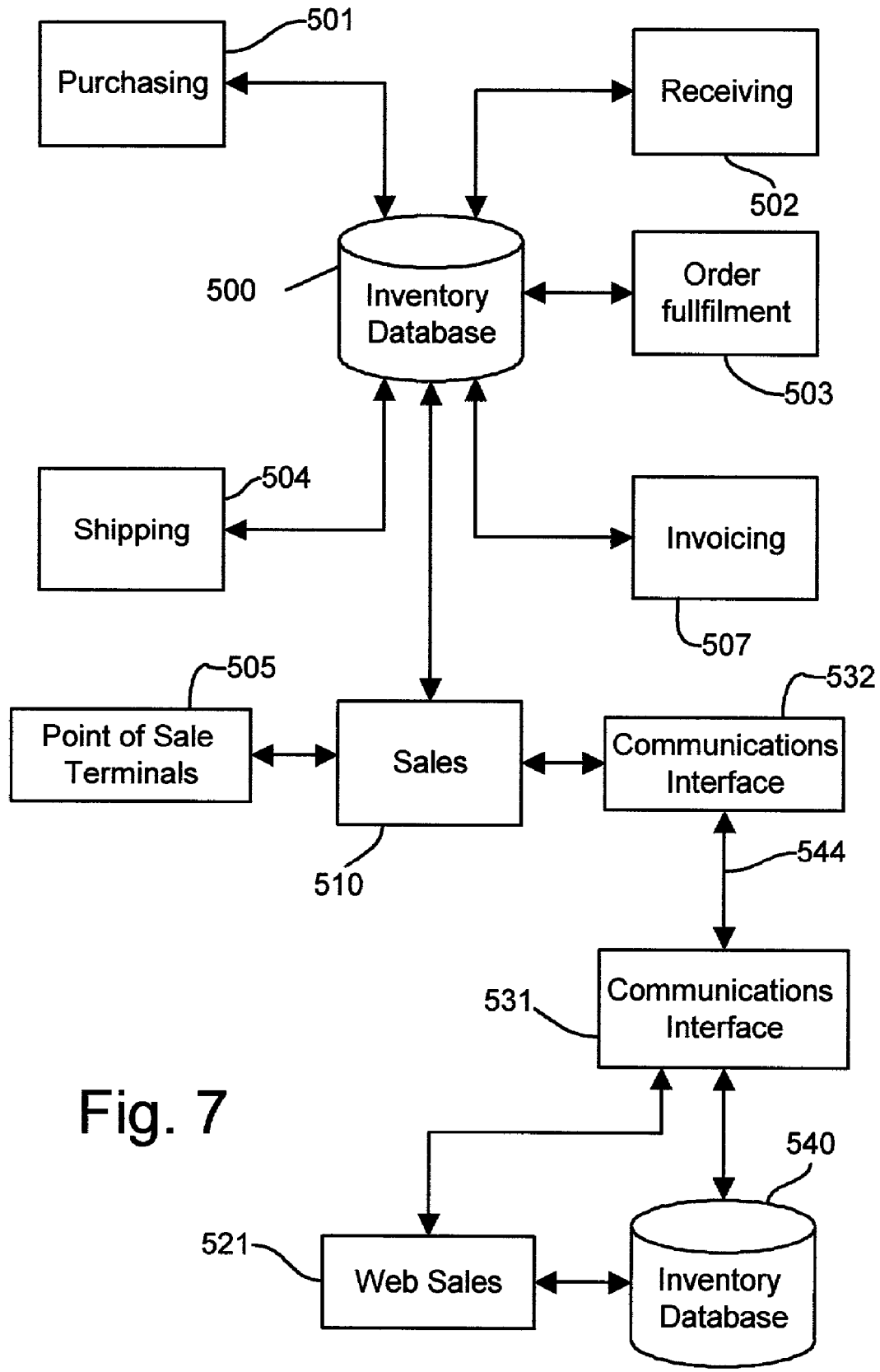
FIGS. 7 and 8 are a block diagrams illustrating the principle components of a typical retailer's inventory control system and the interface between that system and a shared sales server which maintains a parallel but more limited inventory database used during on-line sales transactions.

The relationship between the shared sales server seen at 403 in FIG. 6 and the retailer's inventory control system seen at 420 in FIG. 6 is shown in more detail in FIG. 7 of the drawings. As discussed above, the remote shared sales server operates, from the standpoint of the inventory control system, much in the same way as a conventional point of sale terminal. The other components of the inventory control system include essentially conventional purchasing, receiving, order processing, shipping and invoicing functions described in the literature. See, for example, the texts *Best Practice in Inventory Management,* by Tony Wild, John Wiley & Sons; ISBN: 0471253413 (March 1998) and *Inventory Control and Management* by C. D. J. Waters, John Wiley & Sons; ISBN: 0471930814 (June 1992).

Within the inventory control system, the purchasing module 501 presents printed reports and screen displays which assist purchasing agents to see which products need to be ordered and which vendors need to be contacted to follow up on prior orders, and automates back orders and reorders. The module 502 generates purchase orders, and alerts purchasing agents of urgent or routine product ordering needs by evaluating supplies on hand and estimating the demands for each product to determine if supply levels will fall below the predetermined minimum stock quantities established for each product by the merchant. The purchasing module 501 further creates planned orders based upon a minimum order quantity, order multiple, yield percentage and maximum plan quantities established by the merchant, and alters the purchaser of low product levels automatically. Purchase Orders are generated using screens presented to the purchasing agent which can recall vendor price lists, including price breaks and special promotion pricing. These purchasing functions are typically performed in a bricks-and-mortar retail store or group of stores, and need not be altered to support online sales as contemplated by the present invention.

Similarly, the receiving module 502 accepts inventory control information by capturing data describing incoming orders from vendors, issues inbound receipts and purchase order confirmations, and tracks back orders. Inbound receipts are generated from existing Purchase Orders The order fulfillment unit 503 accepts both conventional sales orders of the type received by mail or telephone, and processes online orders from the shared server (seen at 430 in FIG. 6) in the same way. The unit 503 maintains the visibility of those orders until shipment is completed by identifying orders that need attention, including orders that must be rescheduled or expedited, to insure prompt delivery and to provide order status information to the customer. Customer contact information (phone number, email address or mailing address) from the online shared sales server 430, like similar information obtained by telephone or mail, may be used to automatically issue email notifications or assist the merchant in contacting the customer in other ways to confirm or reschedule orders.

The shipping module 504 is also conventional, and handles outbound shipments, accepts new customer shipping and billing address information, handles partial shipments by identifying items reserved for later shipment, and prints packing slips and bills of lading.

The invoicing module 507 provides invoicing, billing and charging capabilities, printing invoices to be sent to customers. The shared sales server may support billing in several ways: it may simply send orders to the invoicing module 507 including shipping information supplied by the customer using HTML forms; it may verify and accept credit card information and transmit that to the invoicing module 507 so that the actual credit card transaction is between the customer and the retailer, or it may complete the credit card transaction at the shared server, forwarding collected funds together with accounting information to the retailer on a periodic basis.

It is a principle feature of this aspect of the invention that the retail merchant, who already maintains a physical inventory and/or a distribution relationship with manufacturers, as well as an inventory control system for managing its inventory and distribution functions, performs the order fulfillment function using facilities which are shared with those used by conventional "showroom" sales facility. The shared sales server merely processes data, and need not be concerned with the actual selection, purchase or distribution of physical products, nor with the creation of the detailed product information needed by the consumer when making online purchases. Both of these functions remain where they are best performed, with the retailer and the manufacturer respectively.

When sales are performed using conventional point of sale terminals as indicated at 508, a sales module 510 processes the information. The point of sale terminals 508 perform automated sales checkout using a bar code reader to reduce errors and speed customer checkout times, enabling salespeople to focus more on customer service. Sales are manifested by the identification of goods and quantities purchased, and these are reflected in the actual delivery of goods at the point of sale terminal which, in turn, are posted to decrement the on-hand quantity values for the products maintained in the inventory control database 500. If selected products are unavailable at the point of sale, a terminal 508 may commonly be used to place an order for future delivery to an identified customer by posting the order into the database 500 for handling by the purchasing module 501, receiving module 502, order fulfillment module 503, shipping module 504 and invoicing module 507.

Incoming orders from the shared sales server placed on a "web register" are processed in substantially the same way. The order information is obtained from the customer, typically using HTML forms, by the web sales unit seen at 521 in FIG. 7, and the resulting order in the form of customer information, product identification and quantity sold, and related order information is transmitted via the communications interfaces 531 and 532 at the sales server and the remote inventory control system respectively. The communication link 544 advantageously takes the form of an Internet link between the retailer and the remotely located sales server which operates on a transaction by transaction basis. Note that, because both product identification data and on-hand quantity information is available in the database 540 at the shared server, the two can continue to work without continuous connection, with orders taken at the "web register" being transmitted on a batch basis, and with changes to the database of offered product universal product codes and on-hand quantities being posted on a batch basis from the inventory control system to the shared server.

The sales module 510 processes orders from both the point of sale terminals 508 and from the shared sales server. It packages the customer information and the product and quantity sold information for handling by the remaining modules as discussed above, and schedules multiple deliveries as needed when an order can only be partially fulfilled. When web sales are made, on hand quantities are immediately reserved and, if desired, sales of the same products from inventory via the point of sales terminals 508 can be inhibited (although, in practice, if removal of items from the showroom is needed to fill web orders, that should be done promptly to avoid customer confusion).

Figure 8:
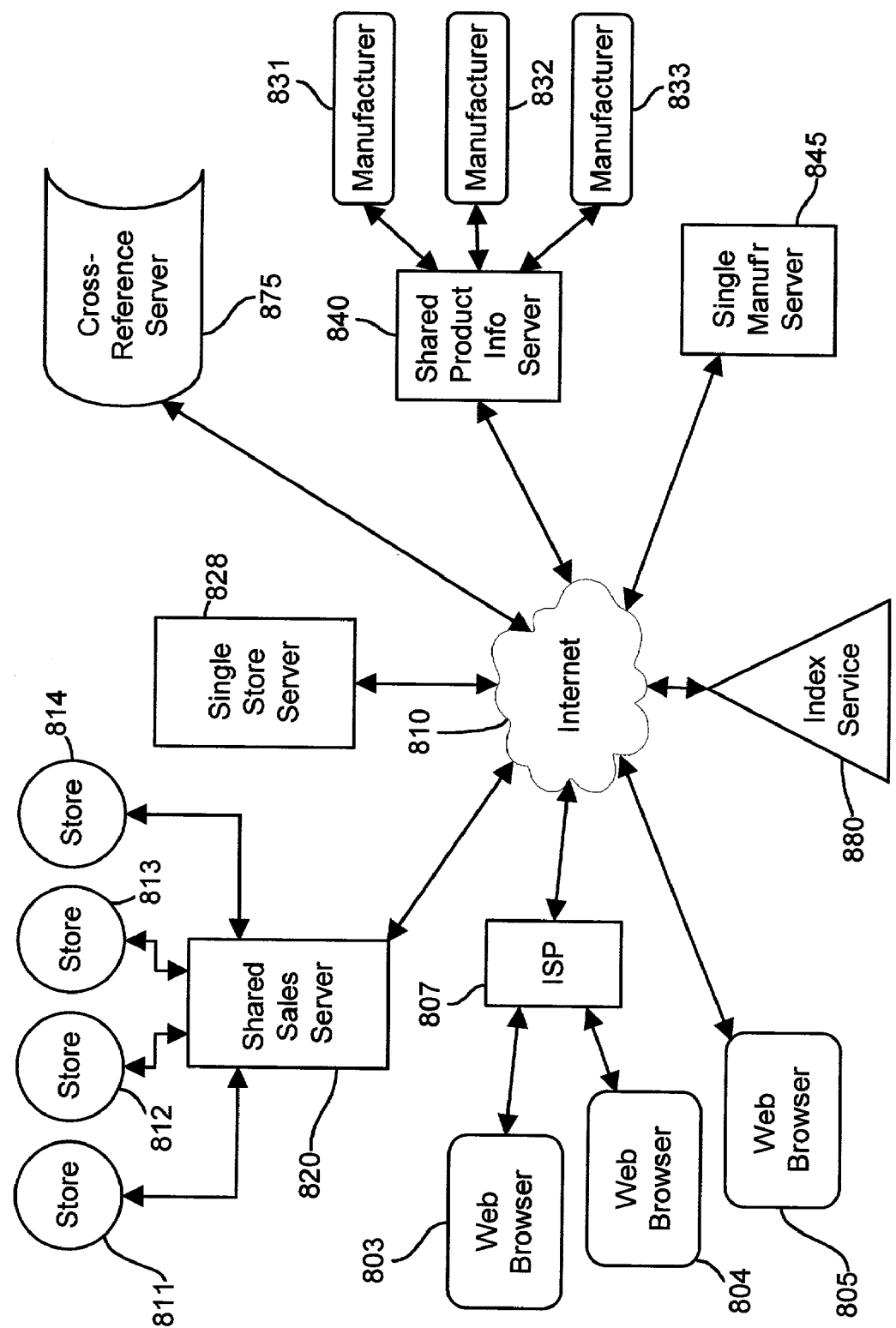

The relationship between retail stores, manufacturers and distributors, product information services and consumers, and the computers connected to the Internet which utilize the invention to serve each of these entities, is depicted in FIG. 8 of the drawings.

Consumers and the general public access information and perform transactions via the Internet using conventional web browsers (i.e. conventional web browser application programs executing on desktop computers or workstations) as exemplified at 803, 804 and 805. Such web browsers typically employ a shared Internet Service Provider (ISP) as indicated at 807 which provides a connection to the Internet 810.

These consumers may view product information and perform sales transactions as contemplated by the present invention by viewing information made available by retail stores 811, 812, 813 and 814 via a shared sales server 820, as well as by a server 825 operated by a single retail store (or chain of stores). The servers 820 and 825 transmit web pages to the web browsers 803–805 which include links to product information which is made available by manufacturers 831, 832 and 833 via a shared product information server 840, and from a server 845 operated by a single manufacturer.

The manufacturers preferably provide product information to their connected server in the form of well-formed Extensible Markup Language (XML) documents which may be validated against a standard Document Type Definition (DTD) to which all such product information documents should conform. The schema to which such documents adhere may be advantageously expressed in the Resource Description Framework (RDF) and Syntax Specification, as noted earlier, to facilitate the evolution of standardized content definitions for product and company information. The shared product information server illustrated at 840, in its simplest form, does nothing more than make Internet accessible data storage space available where smaller manufacturers without their own servers can make product and company information available via the Internet. Even the smallest manufacturer can thus make product and company information available to consumers and retailers worldwide at an insignificant incremental cost. Many such small manufacturers can simply use web hosting space provided free of charge by their existing Internet Service Provider for product and company information storage.

Manufacturers are not, of course, restricted to providing such product information through links from web sites of retailers and others. A manufacturer may use the same information to support its own promotional web site offering such things as product directories, press releases, direct sales to consumers, and any other function and service typically provided by a manufacturer's web site. Indeed, by using a predetermined URL syntax, such as http://cocode.ean/homepage (where "cocode" is the company code assigned to that manufacturer), the home page of the manufacturer of any product can be readily accessed if that product's universal product code is known.

The availability of company information, which may be accessed using the company code portion of a universal product code, also makes it possible for retailers to readily obtain specific information needed to purchase products directly from manufacturers, establish accounts, identify distributors, and the like. The company information which is made available as contemplated by the invention may be used to automatically establish EDI connections and perform EDI transactions between the servers operated on behalf of retail stores and those operated on behalf of manufacturers.

As illustrated at 875 in FIG. 8, the cross-referencing server can be used to by an indexing service to provide searchable product and company information indices and search capabilities. As noted earlier, cross-referencing utility seen at 880 in FIG. 8 may advantageously provide means for accessing the entire contents of its cross-referencing information to a requesting computer, such as a search engine operated by the index service seen at which can then perform conventional "web crawler" indexing of the websites specified by the listed URLs and/or IP addresses, thereby generating complete or partial indexes to all or less than all of the products whose product description locations have been registered. Alternatively, web crawling engines can traverse the links to manufacturers' information found in product listing pages made available by retailers and others.

By storing product and company information in accordance with predetermined schemes, preferably using XML, DTD and RDF techniques as discussed above, indexing services can provide consumers with powerful tools for locating products having selected attributes and for sorting and comparing product based on those attributes. In this way, a consumer can more readily identify particular products which best suit her needs, can view detailed, accurate and up-to-date promotional and specification information on each product directly from the manufacturer, and can then identify the most desirable retail sources for selected products based on price, geography or other criteria. In this way, "bricks and mortar" stores can make their entire existing inventory available for inspection by simply adding a "web register" module to connect their existing bar code checkout and inventory control system with a shared sales server, providing their local customers to "shop at home," make purchases on line, and either pick up or arrange for local delivery of the goods purchased.

Web Services

The present invention may be used to advantage to allow users to directly invoke Web services which relate to or support products designated by universal product codes or to support services offered by manufacturer's designated by the company code portion of those product codes.

The term "Web service" as used herein refers to a software application identified by a Universal Resource Identifier (URI), whose interfaces and binding are capable of being defined, described and discovered by XML artifacts and which supports direct interactions with other software applications using XML based messages via internet-based protocols. Standards-based Web services are already in widespread use and are expected to play a dominate role in the future development of the World Wide Web in general and e-commerce in particular. Detailed information of Web service design techniques may be found, for example, in the texts *Building Web Services with Java: Making Sense of XML, SOAP, WSDL and UDDI* by Steve Graham (Editor) et al. Published by Sams. 1St. Edition (December, 2001) ISBN 0672321815 and *Building Web Services for the Microsoft .NET Platform* by Scott Short, published by Microsoft Press; book and CD-ROM edition (February 2002) ISBN 0735614067.

Web services are invoked by request messages and generate response messages that are typically (although not necessarily) transmitted using the Hypertext Transfer Protocol (HTTP), an application-level protocol used by the World-Wide Web global information system. Version 1.1 (referred to as "HTTP/1.1 ") of that protocol is specified in the Internet Standards Track Request for Comment document RFC 2616, Hypertext Transfer Protocol—HTTP/1.1 (June, 1999). The HTTP protocol is a request/response protocol. A client sends a request to the server in the form of a request method, URI, and protocol version, followed by a MIME-like message containing request modifiers, client information, and body content over a connection with a server which is specified by the Internet protocol address normally supplied by DNS. Request and response messages use the generic Internet message format as defined in the Internet Standards Track Request for Comment document RFC 822, Standard for the Format of AREA Internet Text Messages (August 1982) for transferring entities (the payload of the message). Both types of message consist of a start-line, zero or more header fields (also known as "headers"), an empty line (i.e., a line with nothing preceding the carriage-return, line feed characters) indicating the end of the header fields, and possibly a message-body. The server responds with a status line, including the message's protocol version and a success or error code, followed by a MIME-like message containing server information, entity meat-information, and possible entity-body content.

More specifically, the Web service request message may take the form of an HTTP POST message to the server containing header fields designating the content type as "text/xml" and specifying the content-length. The payload of the HTTP request may be sent in the message body as an XML document which describes the request. By way of example, the following listing illustrates an example of an XML request document imbedded in an HTTP request message that conforms to the Simple Object Access Protocol (SOAP) 1.1, W3C Note, May 8, 2000:

```
POST /ProductWeight HTTP/1.1
Host: 0123456.info
Content-Type: text/xml; charset="utf-8"
Content-Length: nnnn
SOAPAction: "http://0123456.info/getweight"
<SOAP-ENV:Envelope
xmlns:SOAP-ENV="http://schemas.xmlsoap.org/soap/envelope/"
SOAP-ENV:encodingStyle="http://schemas.xml-soap.org/soap/encoding/">
<SOAP-ENV:Body>
<m:GetProductWeight xmlns:m="Some-URI">
<gtin>01234567890123</gtin>
</m:GetProductWeight>
</SOAP-ENV:Body>
</SOAP-ENV:Envelope>
```

In addition to SOAP, other XML protocols which employ XML to form information requests include WebBroker, XML-RPC, BizTalk, ebXML, XMI, WebDAV, ICE and IOTP.

As noted above, Web services are identified and invoked using a unique URI. If that URI includes a domain name which specifies a product code or a company code as contemplated by the present invention, Web services which relate to or support products identified by product codes can be identified by URIs which incorporate product code domain names, and Web services which are offered by manufacturers of those products can be identified by URIs that in include company code domain names, thus permitting those services to be directly and unambiguously invoked using the DNS by anyone knowing the product or company codes. By assigning URIs to Web services in accordance with a standard naming convention (in the same way different kinds of product and company information files were named in the foregoing examples), a manufacturer can readily make needed services directly available to customers others in its supply chain. As illustrated by the SOAP message example above, an application program that performs online sales might programmatically invoke a Web service designated by the URI "http://0123456.info/getweight" to obtain the weight of a product designated by the GTIN 01234567890123, the GTIN being passed in the example as a SOAP message parameter, thus enabling the requesting application program to calculate shipping charges based on product weight. As another example, a Web service which enables customers to obtain product support for a designated product might be invoked using the URI such as "http://12345678901234.info/support." In general, any Web service that might be provided by a remote server with respect to a particular product or manufacturer may be advantageously invoked using the present invention to determine the Internet protocol address to which the service request should be sent as well as to form the domain name and the remainder of the URI which specifies the particular service to be performed at the server accessed at that IP address.

Each Web service offered by a manufacturer may be described by a retrievable XML service description which conforms to Web Services Description Language (WSDL) 1.1, defined by the W3C Note dated Mar. 15, 2001 and/or by using the service identification XML documents published at provider's web sites which conform to WSIL, the Web Services Inspection Language (WS-Inspection) 1.0 Specification (November 2001) available from both IBM and Microsoft. Web services which the manufacturer makes available with respect to particular products or with respect to the company as a whole may be defined in WSIL and WSDL files which are assigned standard resource names in accordance with a predetermined convention and which may accordingly be directly accessed using product code and company code domain names as contemplated by the invention.

WSIL defines an XML based language by which services can be advertised to interested requesters. Unlike WSDL, it is not used to describe the capabilities of the Web Services themselves but instead to "advertise" the availability of Web services. The elements for this language are defined in the schema namespace http://schemas.xmlsoap.org/ws/2001/10/inspection/, which must be referenced by all WSIL documents. WSIL documents may provide, but are not restricted to providing, Web Services lists of Web service descriptions expressed in WSDL. Rather, the WSIL specification is designed to be extensible to other definition types.

A set of standard resource naming conventions allow service requesters to locate WSIL documents on any web site. For example, a WS-Inspection document named "inspection.wsil" should be placed at common entry points for a web site. For example, if the common entry point for a web site is designated by a company code domain name (e.g. http://123456.info/), then the URI of the root WS-Inspection document for that entry point would be http://www.123456.com/inspection.wsil. Similarly, the URI for root WS-Inspection document identifying Web services relating to a product designated by the product code 1234567890123 would be http://1234567890123.info/inspection.wsil. Search engines as Google and Yahoo! may then readily search for WSIL documents at entry points designated by product and company code based domain names to thereby locate and index WSDL Web service descriptions and other resources, permitting users to perform indexed searches for desired Web services and other resources.

Illustrative Example Procedures

Figures 9, 10:
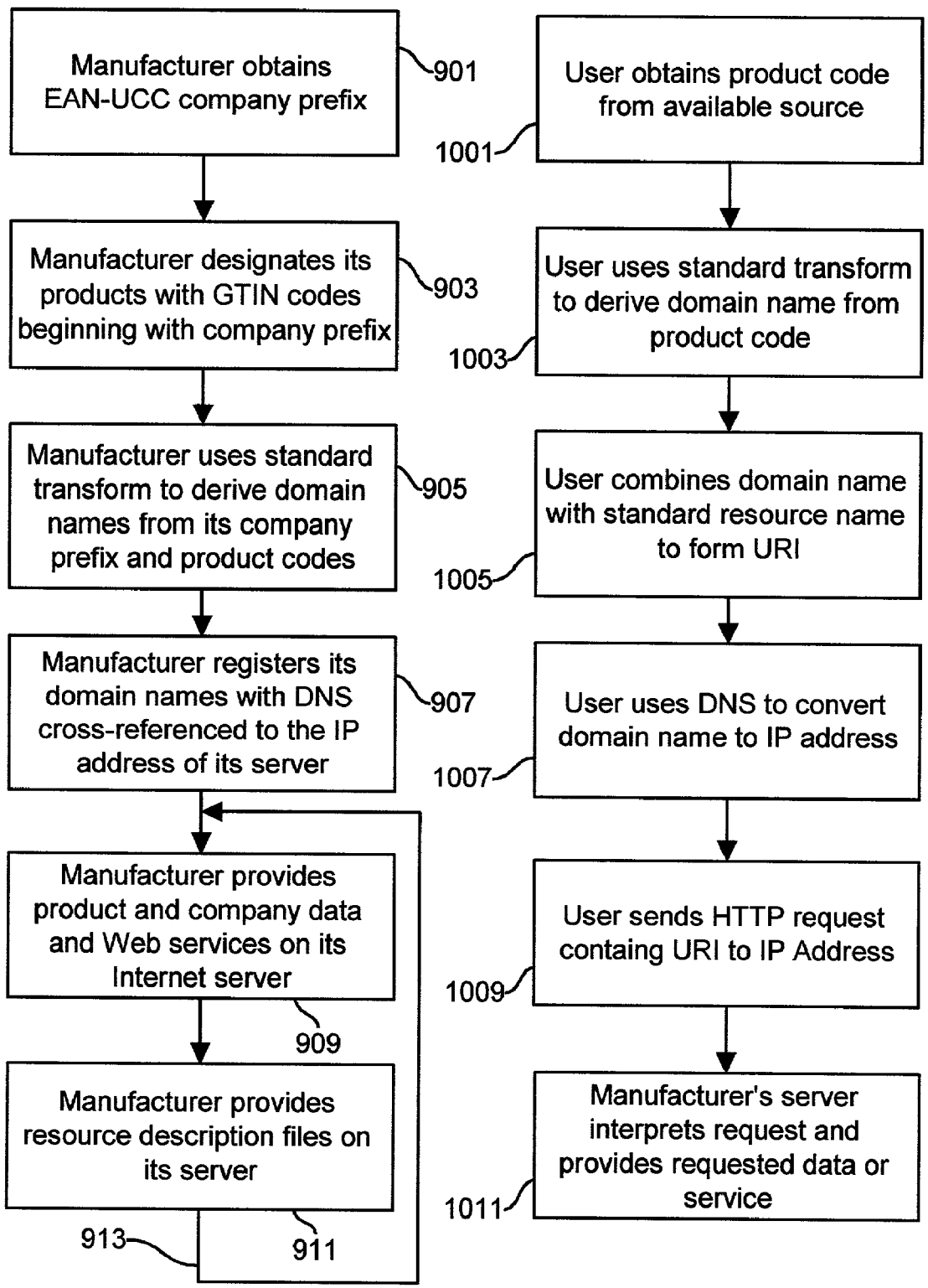
FIGS. 9–12 are flow charts illustrating example procedures which employ the principles of the invention to disseminate information and services relating to manufactured products.

FIG. 9 of the drawings depicts typical steps performed by a manufacturer to disseminate product information and services using the principles of the invention. It should be noted the order in which these steps may vary from the sequence shown in FIG. 9.

As seen in FIG. 9, the manufacturer obtains a company prefix value from the appropriate uniform product code agency, such as the Uniform Code Council, as seen at 901. Thereafter, as seen at 903, the manufacturer designates each of different products it sells using a Global Trade Item Number, a numerical code which is prefixed by the assigned company prefix value and ends with a type identifier number assigned by the manufacturer. The designation typically includes labeling the product or its packaging with a bar code which permits the GTIN to be machine read by a bar code scanner. In addition, the manufacturer uses the GTIN to designate the product in catalogs and documentation (invoices, purchase orders, etc.)

As seen at 905 in FIG. 9, the manufacturer then employs a standard transform to convert its company code prefix and/or the GTINs assigned to its products into corresponding domain names. For example, the standard transform might convert each GTIN, represented as a 14 digit, right justified and zero filled numerical character sequence, and each company code prefix, into a domain name by simply appending the string ".info." to form domain names such as "01234567890123.info" for GTINs and "0123456.info" for company prefixes.

As indicated at 907, the manufacturer then registers each such domain name with the Domain Name System using an authorized domain name registar in the usual way. See *The Domain Name Handbook* by Ellen Rony and Peter Rony, R&D Books (1998) ISBN 0-87930-515-0 for a discussion of conventional DNS registration procedures. As a result of the registrations, cross-references called resource records are placed in the DNS zone files which associate each supplied domain name with a corresponding Internet protocol address (either directly using A or PTR records, or indirectly using aliasing CNAME records which associate the domain name being registered with a canonical domain name that is in turn associated with a specific IP address).

The manufacturer then configures an Internet server that is connected to the Internet and accessed at the IP address or addresses indicated in the domain name registrations to provide product and company data and services upon request as seen at 909. As previously discussed, the server should respond to request messages received at the designated IP address that contain URI's that identify the specific product and/or company code information desired as well as the transport protocol to be used (e.g. http://01234567890123.info promo.xml might identify an XML file containing promotional text describing a product designated by the GTIN 01234567890123 whereas the URI "mailto:support@01234567890123.info" specifies the email address to which an SMTP email message may be sent seeking support for the product designated by the domain name portion of the URI).

In order to facilitate the discovery and invocation of Web services made available by the manufacturer, a Web Services Inspection Language (WSIL) file is preferably placed in the root directory addressed by each company prefix or product code domain name, and by convention has the standard resource name "inspection.wsil." Hence, the manufacture might place the WSIL file designated by the URI "http://0123456.info/inspection.wsil" in the root directory specified by the company prefix derived domain name, and this file would in turn identify the URIs of other WSIL files and WSDL files which describe specific company and product related Web services which can be accessed. In this way, the Web services offered by a manufacturer can be unambiguously invoked without require a UDDI directory search. Other forms of resource description files may be stored at step 911. For example, a simple ASCII text file listing of the GTINs for all products for which data and/or services are available may be stored on the manufacturer's server and accessed at the URI "http://0123456.info/productlist.txt."

As indicated by the return arrow 913 in FIG. 9, the process of adding, revising and deleting individual data and services relating to the manufacturer and its products is ongoing. If the manufacturer is assigned an additional company code prefix, or creates new GTINs which are to be supported by individual domain names, new DNS registrations are not required, and the data and services for products can be revised as needed so that it is up to date. When users dynamically access needed services or data, the most recently updated version will be automatically retrieved. The cache control capabilities built into HTTP may be used to determine whether or not previously retrieved data that has been aggregated or cached at the user location need be updated.

FIG. 10 depicts the basic steps performed by a user to access data or services as contemplated by the invention. As seen at 1001, the user first obtains a product code (e.g. a GTIN) designating a particular product of interest. This product code might be obtained by scanning a barcode on an available product of that type, by keyboarding the product code from any available source, or by using a product code in an available database such as used by a retailer's inventory control system. Note also that the "user" as that term is employed here may be a consumer, a retailer, a distributor, a researcher, or anyone else who may wish to obtain information or services relating to a manufactured product or its manufacturer.

The user then uses the same standard transform that the manufacturer used in step 905 seen in FIG. 9 to convert the available company code into a domain name as seen at 1003. The user then combines this domain name with a standard resource name as indicated at 1005 to form a Uniform Resource Identifier (URI). The user then submits the derived domain name to the DNS at 1007 to obtain the IP address that corresponds to the domain name, and sends a request message containing the URI to this IP address as seen at 1009. The manufacturer's server interprets this request message and performs the requested service and/or returns the requested data to the user at 1011.

Figure 11:
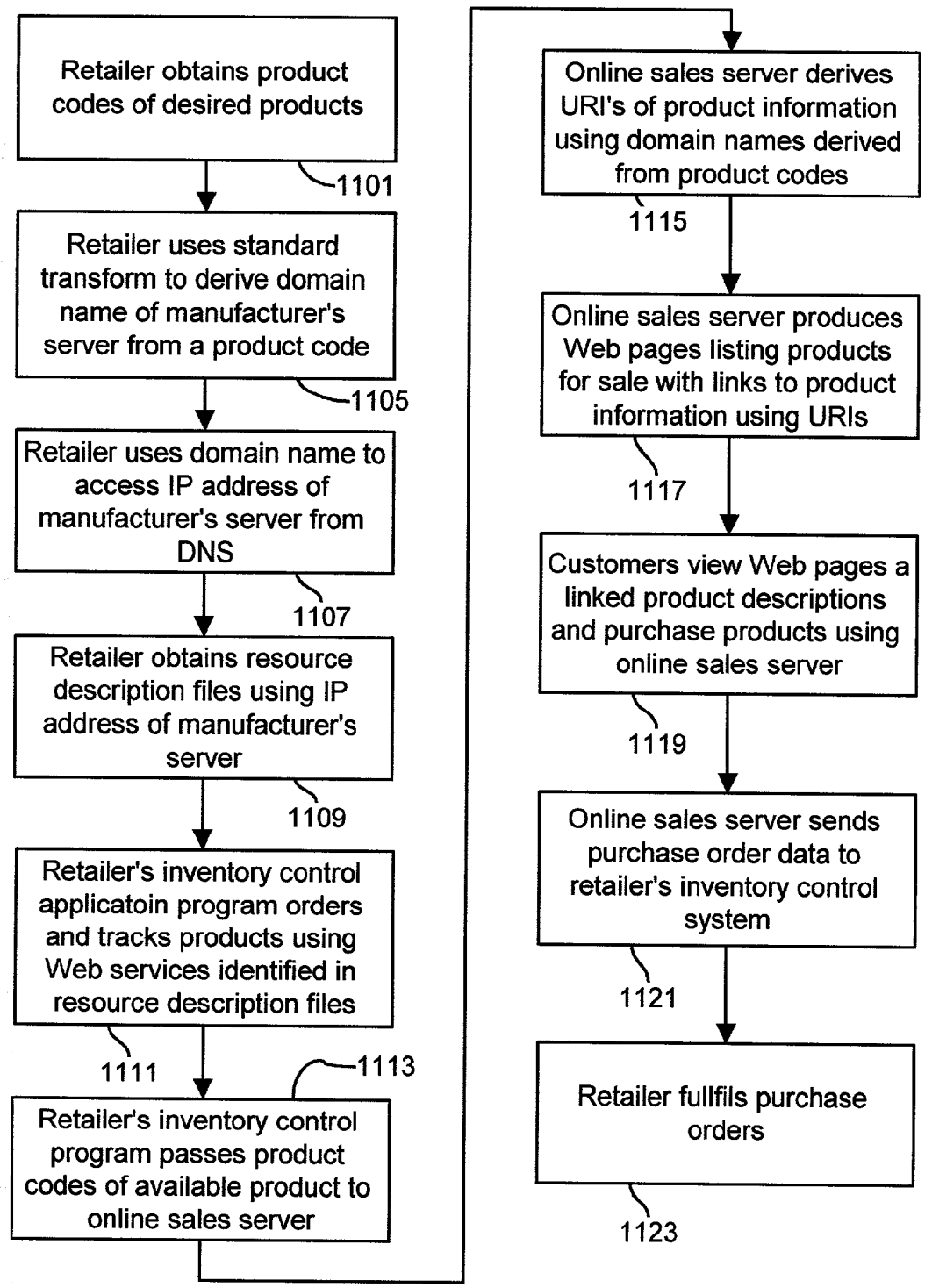

A further example of the use of the invention is shown in the flowchart seen in FIG. 11 which how Web services invoked using the present invention might be used to implement the inventory control and shared sales functions discussed earlier in conjunction with FIG. 7. As seen at 1101 in FIG. 11, the purchasing module 501 obtains universal product codes from the inventory database 500 seen in FIG. 7. In step 1105, the purchasing module uses a standard transform to derive the domain mane of the manufacturer's server from a given product code and then, at step 1107, uses that domain name to obtain the IP address of the manufacturer's server from the DNS, and at step 1109, obtains a resource description file from the manufactuer by sending a request message to that IP address. At step 1111, the purchasing module 501 then determines whether or not Web services are available which would permit automated purchasing of the designate product. If so, the purchasing module 501 transmits a request message to the IP address of the manufacturer sending a SOAP message having a format specified by the resource description files (typically a WSDL document describing the needed product ordering service). Later, when the product is received at the retailer from the manufacturer, the receiving module 502 may invoke a different Web service at the manufacturer to confirm receipt and/or a payment by electronic funds transfer.

When the product is received from the manufacturer, the receiving module 502 updates the inventory database 500 to reflect a new on-hand quantity for that product, and a Web service available at the shared Web sales servier 521 is invoked to update the database 540 maintained by the shared Web sales server 521. As seen at step 1117 in FIG. 11, the online Web sales server 501 uses the product codes in its inventory database 540 to derive the URI's of product information which incorporate the domain names derived from the product codes using the standard transform. The online Web server 521 then transmits Web pages to shoppers which list available products. These Web pages displayed to the shopper at 1119 may include HTML hyperlinks such as "<a href="http://00053800488267.info/promo.html">Lubriderm Moisturizing Lotion(6 fl.oz.)</a> so that, when shopper clicks on the link, detailed product information direct from the manufacturer is dynamically displayed on the shopper's Web browser (without either the retailer or the Web sales server ever needing to store the detailed product information).

As seen at 1121, when a customer purchases a given product, the Web sales server updates the on-hand quantity in its own database 540 and transmits order information, including the customer's shipping address, to the retail sales system so that, as seen at 1123, the order fulfillment module 503 can ship ordered goods and update the inventory database 500.

Figure 12:
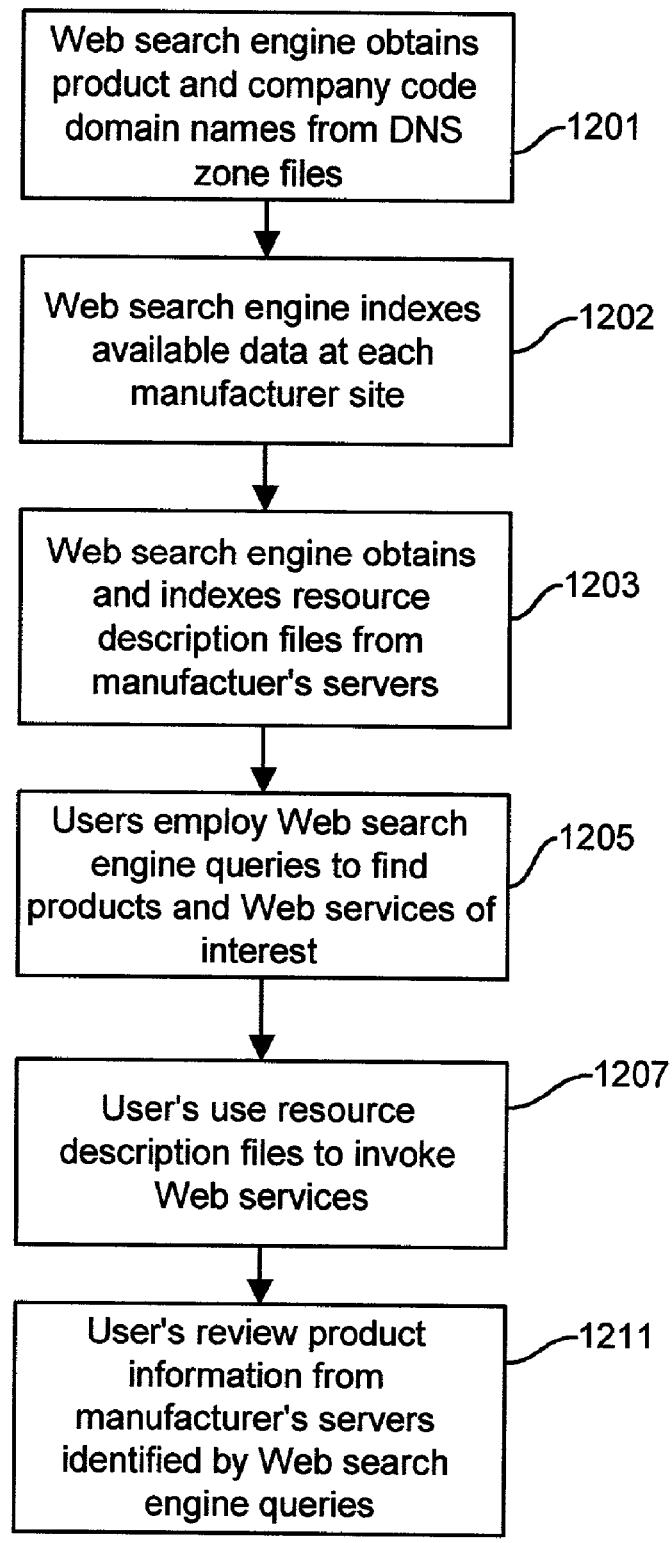

A still further example use of the invention is illustrated by the flowchart of FIG. 12. A Web search engine (such as the Web indices google.com or yahoo.com) obtains product and company code domain name registration data from the DNS zone files as seen at 1201. The search engine "walks" through the available and indexable product and copy data at each site as indicated at 1202. In addition, as seen at 1203, the search engine may fetch the available resource description files from each server identified by the DNS resource records and also index the Web services and other resources identified and described in the resource description files.

Thereafter, as seen at 1205, users may employ the Web search engine to locate and access desired information. Having identified a potentially useful source of information, the user may access resource description files (such as Web Service Description Language documents) to obtain the information need to bind to and invoke a particular Web service as seen at 1207.

CONCLUSION

It should be understood that the methods and apparatus described above are merely illustrative applications of the principles of the present invention. Numerous modifications may be made by those skilled in the art without departing from the true spirit and scope of the invention.

What is claimed is:

1. A new use for the Internet Domain Name System which comprises, in combination, the steps of:
    establishing a plurality of separate hosts connected to the Internet, each of said hosts providing data relating to one or more products, each of said products being designated by a unique universal product code value, and each of said hosts being designated by a unique Internet address,
    storing cross-references in the Internet Domain Name System, each of said cross-references establishing a relationship between a domain name that incorporates at least a predetermined portion of a given one of said product code values and a corresponding Internet address of the host computer that provides data relating to the product designated by said given one of said product code values, and
    retrieving data via the Internet that relates to a particular product designated by a particular universal product code value by performing the steps of:
    transforming said particular universal product code value into a destination domain name that incorporates at least said predetermined portion of said particular one of said universal product code values,
    using the Internet Domain Name System to convert said destination domain name into the destination Internet address that corresponds to said destination domain name, and
    retrieving data relating to said particular product via the Internet from the host designated by said destination Internet address.

2. The new use for the Internet Domain Name System set forth in claim 1 wherein said data relating to said particular product is expressed in Extensible Markup Language.

3. The new use for the Internet Domain Name System set forth in claim 2 wherein said step of retrieving data relating to said particular product comprises requesting the performance of a Web service provided by said host designated by said domain name.

4. The new use forte Internet Domain Name System set forth in claim 1 wherein said step of retrieving data relating to said particular product from the host designated by said destination domain name comprises, in combination,
    forming a Uniform Resource Identifier which includes said destination domain name and further specifies a specific resource provided by said host designated by said domain name,
    transmitting a data request message containing said Uniform Resource Identifier to said destination Internet address, and
    receiving response data transmitted by said host designated by said domain name in response to said data request message.

5. The new use for the Internet Domain Name System set forth in claim 4 wherein said step of forming a Uniform Resource Identifier which includes said destination domain name and further specifies a specific resource provided by said host designated by said domain name includes the substep of retrieving resource identification data from said host designated by said domain name.

6. The new use for the Internet Domain Name System set forth in claim 5 wherein said resource identification data is expressed in the Web Services Description Language.

7. The new use for the Internet Domain Name System set forth in claim 5 wherein said resource identification data is expressed in the Web Services Inspection Language.

8. The new use for the Internet Domain Name System set forth in claim 1 wherein said particular universal product code value is a Global Trade Item Number.

9. A system for disseminating information relating to a plurality of different manufactured products, each given one of said products being designated by a unique universal product code value that includes a numeric company code designating the manufacturer of said given one of said products said system comprising, in combination:
    a plurality of different host computers each of which is operated on behalf of one or more of manufacturers and each of which comprises storage means for accepting and staring information about at least one of said products and each of which has an entry point connection to the Internet tat is uniquely identified by an Internet protocol address for receiving and responding to Internet messages requesting information relating to said at least one of said products,
    registration means for storing cross-references in the Internet Domain Name System, each of said cross-references specifying an association between a company code domain name and a corresponding Internet protocol address wherein said company code domain name comprises an alphanumeric character string comprising one of said numeric company codes designating a particular manufacturer and predetermined characters concatenated with said one said numeric company codes, and wherein said corresponding Internet protocol address identifies the particular entry point connection to a particular one of said host computers operated on behalf of said particular manufacturer that receives and responds to Internet messages requesting information relating to products manufactured by said particular manufacturer, means for retrieving information about a selected one of said products that is designated by a selected one of said universal product code values comprising:

means for deriving a target company code domain name from the numeric company code in a selected one of said universal product code values, means for transmitting said target product code domain name to the Internet Domain Name System to obtain the corresponding target Internet protocol address specified by one of said cross-references, and means for transmitting an Internet message requesting information relating to said selected one of said products to said corresponding target Internet protocol address.

10. The system set forth in claim 9 wherein said means for retrieving information about a selected one of said products that is designated by a selected one of said universal product code values further comprises means for forming a Uniform Resource Identifier which includes said target product code domain name and for including said Uniform Resource Identifier in said Internet message requesting information.

11. The system set forth in claim 10 wherein said means for forming a Uniform Resource Identifier which includes said destination domain name further comprises means for retrieving resource identification data from said host designated by said product code domain name.

12. The system as set forth in claim 10 wherein said Uniform Resource Identifier specifies a Web service.

13. The system set forth in claim 12 wherein said means for forming a Uniform Resource Identifier which includes said destination domain name further comprises means for retrieving resource identification data from said host designated by said product code domain name.

14. The system set forth in claim 13 wherein said resource identification data is expressed in the Web Services Description Language.

15. The system set forth in claim 13 wherein said resource identification data is expressed in the Web Services Inspection Language.

16. The system set forth in claim 9 wherein said particular universal product code value is a Global Trade Item Number.

17. A system for distributing information via the Internet relating to a manufactured product designated by a specific universal product code value that includes numeric company code characters that designate the manufacturer of said manufactured product, said system comprising, in combination:

means for storing said information at a computing host accessible via the Internet at a specific Internet protocol address, a first source of a specific universal product code value that designates a specific product, means coupled to said first source for deriving a domain name character string that includes numeric company code characters that designates the manufacturer of said specific product from said specific universal product code value in accordance with a predetermined translation process, means for storing a cross-reference in the Internet Domain Name System, said cross-reference specifying an association between said domain name character string and said specific Internet protocol address, and utilization means coupled to the Internet comprising:

a second source of said specific universal product code value, means coupled to said second source for deriving a target domain name character string from said specific universal product code value in accordance with said predetermined translation process, means for transmitting said target domain name character string to the Internet Domain Name System to obtain said specific Internet protocol address, and means for transmitting a request message via the Internet to said specific Internet protocol address to obtain said information relating to said manufactured product designated by said specific universal product code value.

18. The system set forth in claim 17 wherein said means for retrieving information about a selected one of said products that is designated by a selected one of said universal product code values further comprises means for forming a Uniform Resource Identifier which includes said target domain name character string and for including said Uniform Resource Identifier in said Internet message requesting information.

19. The system set forth in claim 18 wherein said means for forming a Uniform Resource Identifier which includes said target domain name character string further comprises means for retrieving resource identification data from said host designated by said target domain name character string.

20. The system as set forth in claim 18 wherein said Uniform Resource Identifier specifies a Web service.

21. The system set forth in claim 20 wherein said means for forming a Uniform Resource Identifier which includes said target domain name character string further comprises means for retrieving resource description data from said host designated by said target domain name character string.

22. The system set forth in claim 21 wherein said resource description data describes said Web service and is expressed in the Web Services Description Language.

23. The system set forth in claim 21 wherein said resource description data identifies said Web service and is expressed in the Web Services Inspection Language.

24. The system set forth in claim 20 wherein said particular universal product code value is a numeric Global Trade Item Number.

* * * * *